US009421242B2

(12) United States Patent
Rodriguez et al.

(10) Patent No.: US 9,421,242 B2
(45) Date of Patent: Aug. 23, 2016

(54) METHODS AND MATERIALS FOR REDUCING THE SEVERITY OF VIRAL INFECTIONS

(71) Applicant: Mayo Foundation for Medical Education and Research, Rochester, MN (US)

(72) Inventors: Moses Rodriguez, Rochester, MN (US); Allan J. Bieber, Rochester, MN (US); Arthur E. Warrington, Jr., Rochester, MN (US); Meghan McGee Painter, Rochester, MN (US); Eric M. Poeschla, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/156,275

(22) Filed: Jan. 15, 2014

(65) Prior Publication Data

US 2014/0206754 A1 Jul. 24, 2014

Related U.S. Application Data

(60) Provisional application No. 61/754,126, filed on Jan. 18, 2013.

(51) Int. Cl.
*C12N 15/86* (2006.01)
*A61K 38/16* (2006.01)

(52) U.S. Cl.
CPC ..... *A61K 38/162* (2013.01); *C12N 2740/16043* (2013.01); *C12N 2770/32222* (2013.01); *C12N 2770/32232* (2013.01); *C12N 2800/22* (2013.01)

(58) Field of Classification Search
None
See application file for complete search history.

(56) References Cited

PUBLICATIONS

Phua, et al. (2013) "Transfection Efficiency and Transgene Expression Kinetics of mRNA Delivered in Naked and Nanoparticle Format", Journal of Controlled Release, 166(3): 227-33.*
Kerkvliet, et al. (2011) "Antiviral Effects of a Transgenic RNA-Dependent RNA Polymerase", Journal of Virology, 85(1): 621-25.*

Parisien, et al. (2002) "STAT2 Acts as a Host Range Determinant for Species-Specific Paramyxovirus Interferon Antagonism and Simian Virus 5 Replication", Journal of Virology, 76(13): 6413-41.* http://en.wikipedia.org/wiki/Mammal, published by Wikipedia, the free Encyclopedia, SanFrancisco, CA, downloaded Feb. 6, 2015, no author listed, no journal, no volume, no issue, 14 pages long.*

Shen, et al. (2008) "Picornavirus genome replication: Identification of the surface of the poliovirus (PV) 3C dimer that interacts with PV 3Dpol during VPg uridylylation and construction of a structural model for the PV 3C2-3Dpol complex", Journal of Biological Chemistry, 283(2): 875-88.*

Denton, et al. (2010) "Systemic Administration of Antiretrovirals Prior to Exposure Prevents Rectal and Intravenous HIV-1 Transmission in Humanized BLT Mice", PLoS One, 5(1): e8829 (pp. 1-11).* http://www.uniprot.org/uniprot/O93182, Author unknown, No journal, No Issue number, Published online by Uniprot Consortium, Washington, DC, USA, downloaded Jun. 21, 2015, 12 pages long.*

GenBank® accession #M20301, "Theiler murine encephalomyelitis virus, complete genome," Aug. 3, 1993, 4 pages.
GenBank® accession NC_001366, "Theilovirus, complete genome," Mar. 9, 2011, 5 pages.
GenBank® accession NC_001479, "Encephalomyocarditis virus, complete genome," Jun. 1, 2012, 5 pages.
GenBank® accession NC_002058, "Poliovirus, complete genome," Dec. 8, 2008, 7 pages.
GenBank® accession NC_003982, "Equine rhinitis A virus, complete genome," Feb. 5, 2011, 5 pages.
GenBank® accession NC_004004, "Foot-and-mouth disease virus—type O, complete genome," Nov. 30, 2009, 5 pages.
GenBank® accession NC_009448, "Saffold virus, complete genome," Apr. 24, 2008, 4 pages.
GenBank® accession NM_001001892, "Mus musculus histocompatibility 2, K1, K region (H2-K1), transcript variant 1, mRNA," Nov. 11, 2012, 4 pages.
GenBank® accession NM_001013371, "Mus musculus deltex 3-like (*Drosophila*) (Dtx31), mRNA," Jun. 30, 2012, 4 pages.
GenBank® accession NM_001032731, "*Homo sapiens* 2'-5'-oligoadenylate synthetase 2, 69/71kDa (OAS2), transcript variant 3, mRNA," Oct. 13, 2012, 3 pages.

GenBank® accession NM_001033207, "Mus musculus NLR family, CARD domain containing 5 (N1rc5), mRNA," Sep. 30, 2012, 10 pages.

GenBank® accession NM_001037713, "Mus musculus XIAP associated factor 1 (Xaf1), mRNA," Jul. 1, 2012, 3 pages.
GenBank® accession NM_001039160, "Mus musculus GTPase, very large interferon inducible 1 (Gvin1), transcript variant 2, mRNA," Jun. 29, 2012, 5 pages.
GenBank® accession NM_001039530, "Mus musculus poly (ADP-ribose) polymerase family, member 14 (Parp14), mRNA," Jul. 22, 2012, 6 pages.
GenBank® accession NM_001039646, "Mus musculus guanylate-binding protein 10 (Gbp10), mRNA," Jul. 3, 2012, 3 pages.

(Continued)

*Primary Examiner* — Robert M Kelly
(74) *Attorney, Agent, or Firm* — Fish & Richardson P.C.

(57) ABSTRACT

This document relates to methods and materials involved in treating and/or preventing and/or reducing the severity of a viral infection present in a mammal. For example, methods for increasing expression of an Oas gene family polypeptide, an Ifit gene family polypeptide, an Isg15 polypeptide, a Rig-1 polypeptide, a Mda5 polypeptide, and a Mx1 polypeptide in mammals using a lentiviral vector comprising nucleic acid encoding a picornavirus 3Dpol polypeptide (or a fragment thereof) are provided.

7 Claims, 8 Drawing Sheets

(56) References Cited

PUBLICATIONS

GenBank® accession NM_001081215, "Mus musculus DEAD (Asp-Glu-Ala-Asp) box polypeptide 60 (Ddx60), mRNA," Aug. 25, 2012, 6 pages.

GenBank® accession NM_001083312, "Mus musculus guanylate binding protein 7 (Gbp7), mRNA," Jun. 30, 2012, 4 pages.

GenBank® accession NM_001143689, "Mus musculus histocompatibility 2, Q region locus 4 (H2-Q4), mRNA," Jun. 28, 2012, 3 pages.

GenBank® accession NM_001144925, "Homo sapiens myxovirus (influenza virus) resistance 1, interferon-inducible protein p78 (mouse) (MX1), transcript variant 1, mRNA," Sep. 30, 2012, 6 pages.

GenBank® accession NM_001145164, "Mus musculus T cell specific GTPase 2 (Tgtp2), mRNA," Jul. 3, 2012, 3 pages.

GenBank® accession NM_001146007, "Mus musculus tripartite motif-containing 12C (Trim12c), transcript variant 1, mRNA," Jul. 1, 2012, 3 pages.

GenBank® accession NM_001146275, "Mus musculus interferon inducible GTPase 1 (Iigp1), transcript variant 2, mRNA," Nov. 18, 2012, 4 pages.

GenBank® accession NM_001159301, "Mus musculus lectin, galactose binding, soluble 9 (Lgals9), transcript variant 2, mRNA," Sep. 2, 2012, 4 pages.

GenBank® accession NM_001159417, "Mus musculus interferon regulatory factor 9 (Irf9), transcript variant 1, mRNA," Jun. 28, 2012, 4 pages.

GenBank® accession NM_001162883, "Mus musculus apolipoprotein L 9a (Apol9a), transcript variant 2, mRNA," Jun. 30, 2012, 2 pages.

GenBank® accession NM_001163540, "Mus musculus plectin (Plec), transcript variant 13, mRNA," Apr. 29, 2012, 12 pages.

GenBank® accession NM_001164477, "Mus musculus interferon induced with helicase C domain 1 (Ifih1), transcript variant 2, mRNA," Jun. 16, 2012, 5 pages.

GenBank® accession NM_001167743, "Mus musculus schlafen 8 (Slfn8), transcript variant 2, mRNA," Aug. 15, 2011, 2 pages.

GenBank® accession NM_001167828, "Mus musculus tripartite motif-containing 30D (Trim30d), transcript variant 2, mRNA," Jun. 30, 2012, 3 pages.

GenBank® accession NM_001198560, "Mus musculus histocompatibility 2, Q region locus 7 (H2-Q7), transcript variant 2, mRNA," Nov. 28, 2011, 3 pages.

GenBank® accession NM_001547, "Homo sapiens interferon-induced protein with tetratricopeptide repeats 2 (IFIT2), mRNA," Oct. 14, 2012, 5 pages.

GenBank® accession NM_001548, "Homo sapiens interferon-induced protein with tetratricopeptide repeats 1 (IFIT1), transcript variant 1, mRNA," Nov. 17, 2012, 5 pages.

GenBank® accession NM_001549, "Homo sapiens interferon-induced protein with tetratricopeptide repeats 3 (IFIT3), transcript variant 1, mRNA," Oct. 14, 2012, 5 pages.

GenBank® accession NM_002463, "Homo sapiens myxovirus (influenza virus) resistance 2 (mouse) (MX2), mRNA," Jun. 2, 2012, 5 pages.

GenBank® accession NM_002759, "Homo sapiens eukaryotic translation initiation factor 2-alpha kinase 2 (EIF2AK2), transcript variant 1, mRNA," Oct. 21, 2012, 6 pages.

GenBank® accession NM_003733, "Homo sapiens 2'-5'-oligoadenylate synthetase-like (OASL), transcript variant 1, mRNA," Jun. 27, 2012, 4 pages.

GenBank® accession NM_004335, "Homo sapiens bone marrow stromal cell antigen 2 (BST2), mRNA," Nov. 10, 2012, 3 pages.

GenBank® accession NM_005101, "Homo sapiens ISG15 ubiquitin-like modifier (ISG15), mRNA," Oct. 7, 2012, 4 pages.

GenBank® accession NM_006187, "Homo sapiens 2'-5'-oligoadenylate synthetase 3, 100kDa (OAS3), mRNA," Jun. 2, 2012, 6 pages.

GenBank® accession NM_008326, "Mus musculus immunity-related GTPase family M member 1 (Irgm1), mRNA," Jul. 22, 2012, 4 pages.

GenBank® accession NM_008327, "Mus musculus interferon activated gene 202B (Ifi202b), transcript variant 1, mRNA," Jun. 28, 2012, 4 pages.

GenBank® accession NM_008330, "Mus musculus interferon gamma inducible protein 47 (Ifi47), mRNA," Jun. 28, 2012, 3 pages.

GenBank® accession NM_008331, "Mus musculus interferon-induced protein with tetratricopeptide repeats 1 (Ifit1), mRNA," Jun. 28, 2012, 4 pages.

GenBank® accession NM_008332, "Mus musculus interferon-induced protein with tetratricopeptide repeats 2 (Ifit2), mRNA," Jun. 28, 2012, 5 pages.

GenBank® accession NM_009099, "Mus musculus tripartite motif-containing 30A (Trim30a), mRNA," Jun. 24, 2012, 4 pages.

GenBank® accession NM_009283, "Mus musculus signal transducer and activator of transcription 1 (Stat1), transcript variant 2, mRNA," Sep. 15, 2012, 5 pages.

GenBank® accession NM_009546, "Mus musculus tripartite motif-containing 25 (Trim25), mRNA," Jun. 30, 2012, 5 pages.

GenBank® accession NM_009735, "Mus musculus beta-2 microglobulin (B2m), mRNA," Jun. 28, 2012, 3 pages.

GenBank® accession NM_010156, "Mus musculus sterile alpha motif domain containing 9-like (Samd91), mRNA," Jun. 30, 2012, 4 pages.

GenBank® accession NM_010260, "Mus musculus guanylate binding protein 2 (Gbp2), mRNA," Jun. 28, 2012, 4 pages.

GenBank® accession NM_010380, "Mus musculus histocompatibility 2, D region locus 1 (H2-D1), mRNA," Jun. 28, 2012, 4 pages.

GenBank® accession NM_010398, "Mus musculus histocompatibility 2, T region locus 23 (H2-T23), mRNA," Jun. 28, 2012, 4 pages.

GenBank® accession NM_010501, "Mus musculus interferon-induced protein with tetratricopeptide repeats 3 (Ifit3), mRNA," Jun. 28, 2012, 3 pages.

GenBank® accession NM_010724, "Mus musculus proteasome (prosome, macropain) subunit, beta type 8 (large multifunctional peptidase 7) (Psmb8), mRNA," Jun. 28, 2012, 3 pages.

GenBank® accession NM_010738, "Mus musculus lymphocyte antigen 6 complex, locus A (Ly6a), mRNA," Jun. 17, 2012, 3 pages.

GenBank® accession NM_010846, "Mus musculus myxovirus (influenza virus) resistance 1 (Mx1), mRNA," Jun. 28, 2012, 4 pages.

GenBank® accession NM_011150, "Mus musculus lectin, galactoside-binding, soluble, 3 binding protein (Lgals3bp), mRNA," Jun. 28, 2012, 4 pages.

GenBank® accession NM_011163, "Mus musculus eukaryotic translation initiation factor 2-alpha kinase 2 (Eif2ak2), mRNA," Jun. 28, 2012, 5 pages.

GenBank® accession NM_011331, "Mus musculus chemokine (C-C motif) ligand 12 (Ccl12), mRNA," Jun. 28, 2012, 3 pages.

GenBank® accession NM_011854, "Mus musculus 2'-5' oligoadenylate synthetase-like 2 (Oasl2), mRNA," Jun. 28, 2012, 3 pages.

GenBank® accession NM_011909, "Mus musculus ubiquitin specific peptidase 18 (Usp18), mRNA," Jun. 28, 2012, 4 pages.

GenBank® accession NM_013585, "Mus musculus proteasome (prosome, macropain) subunit, beta type 9 (large multifunctional peptidase 2) (Psmb9), mRNA," Jun. 17, 2012, 3 pages.

GenBank® accession NM_013606, "Mus musculus myxovirus (influenza virus) resistance 2 (Mx2), mRNA," Jun. 28, 2012, 4 pages.

GenBank® accession NM_013653, "Mus musculus chemokine (C-C motif) ligand 5 (Ccl5), mRNA," Jun. 28, 2012, 3 pages.

GenBank® accession NM_014314, "Homo sapiens DEAD (Asp-Glu-Ala-Asp) box polypeptide 58 (DDX58), mRNA," Jun. 28, 2012, 6 pages.

GenBank® accession NM_015783, "Mus musculus ISG15 ubiquitin-like modifier (Isg15), mRNA," Jun. 17, 2012, 3 pages.

GenBank® accession NM_016816, "Homo sapiens 2'-5'-oligoadenylate synthetase 1, 40/46kDa (OAS1), transcript variant 1, mRNA," Jun. 27, 2012, 4 pages.

GenBank® accession NM_016850, "Mus musculus interferon regulatory factor 7 (Irf7), transcript variant 1, mRNA," Jun. 29, 2012, 4 pages.

(56) References Cited

OTHER PUBLICATIONS

GenBank® accession NM_018734, "Mus musculus guanylate binding protein 3 (Gbp3), mRNA," Jun. 29, 2012, 4 pages.
GenBank® accession NM_018738, "Mus musculus interferon gamma induced GTPase (Igtp), mRNA," Jun. 28, 2012, 4 pages.
GenBank® accession NM_018866, "Mus musculus chemokine (C-X-C motif) ligand 13 (Cxcl13), mRNA," Jun. 29, 2012, 4 pages.
GenBank® accession NM_019440, "Mus musculus immunity-related GTPase family M member 2 (Irgm2), mRNA," Jun. 29, 2012, 3 pages.
GenBank® accession NM_020119, "*Homo sapiens* zinc finger CCCH-type, antiviral 1 (ZC3HAV1), transcript variant 1, mRNA," Jun. 29, 2012, 7 pages.
GenBank® accession NM_021034, "*Homo sapiens* interferon induced transmembrane protein 3 (IFITM3), transcript variant 1, mRNA," Jun. 27, 2012, 3 pages.
GenBank® accession NM_021274, "Mus musculus chemokine (C-X-C motif) ligand 10 (Cxcl10), mRNA," Jun. 28, 2012, 3 pages.
GenBank® accession NM_021384, "Mus musculus radical S-adenosyl methionine domain containing 2 (Rsad2), mRNA," Jun. 29, 2012, 4 pages.
GenBank® accession NM_022168, "*Homo sapiens* interferon induced with helicase C domain 1 (IFIH1), mRNA," Jun. 29, 2012, 5 pages.
GenBank® accession NM_023386, "Mus musculus receptor transporter protein 4 (Rtp4), mRNA," Jun. 29, 2012, 3 pages.
GenBank® accession NM_023738, "Mus musculus ubiquitin-like modifier activating enzyme 7 (Uba7), mRNA," Jun. 29, 2012, 5 pages.
GenBank® accession NM_025378, "Mus musculus interferon induced transmembrane protein 3 (Ifitm3), mRNA," Jun. 29, 2012, 4 pages.
GenBank® accession NM_025992, "Mus musculus hect domain and RLD 6 (Herc6), mRNA," Jun. 29, 2012, 5 pages.
GenBank® accession NM_026790, "Mus musculus interferon, alpha-inducible protein 27 like 1 (Ifi2711), transcript variant 1, mRNA," Jun. 29, 2012, 3 pages.
GenBank® accession NM_027320, "Mus musculus interferon-induced protein 35 (Ifi35), mRNA," Jun. 29, 2012, 3 pages.
GenBank® accession NM_028421, "Mus musculus zinc finger CCCH type, antiviral 1 (Zc3hav1), transcript variant 1, mRNA," Jun. 30, 2012, 5 pages.
GenBank® accession NM_029499, "Mus musculus membrane-spanning 4-domains, subfamily A, member 4C (Ms4a4c), mRNA," Jun. 29, 2012, 3 pages.
GenBank® accession NM_029509, "Mus musculus guanylate-binding protein 8 (Gbp8), mRNA," Jun. 29, 2012, 3 pages.
GenBank® accession NM_029803, "Mus musculus interferon, alpha-inducible protein 27 like 2A (Ifi2712a), mRNA," Jun. 29, 2012, 3 pages.
GenBank® accession NM_030150, "Mus musculus DEXH (Asp-Glu-X-His) box polypeptide 58 (Dhx58), mRNA," Jun. 30, 2012, 4 pages.
GenBank® accession NM_030253, "Mus musculus poly (ADP-ribose) polymerase family, member 9 (Parp9), mRNA," Jun. 30, 2012, 3 pages.
GenBank® accession NM_033616, "Mus musculus component of Sp100-rs (Csprs), mRNA," Jun. 30, 2012, 3 pages.
GenBank® accession NM_080657, "*Homo sapiens* radical S-adenosyl methionine domain containing 2 (RSAD2), mRNA," Jun. 30, 2012, 4 pages.
GenBank® accession NM_133871, "Mus musculus interferon-induced protein 44 (Ifi44), mRNA," Jun. 30, 2012, 3 pages.
GenBank® accession NM_139198, "Mus musculus placenta-specific 8 (Plac8), mRNA," Jun. 30, 2012, 3 pages.
GenBank® accession NM_145209, "Mus musculus 2'-5' oligoadenylate synthetase-like 1 (Oasl1), mRNA," Jun. 30, 2012, 3 pages.
GenBank® accession NM_145211, "Mus musculus 2'-5' oligoadenylate synthetase 1A (Oas1a), mRNA," Jul. 1, 2012, 4 pages.
GenBank® accession NM_145226, "Mus musculus 2'-5' oligoadenylate synthetase 3 (Oas3), mRNA," Jul. 1, 2012, 4 pages.
GenBank® accession NM_145227, "Mus musculus 2'-5' oligoadenylate synthetase 2 (Oas2), mRNA," Jul. 21, 2012, 4 pages.
GenBank® accession NM_172689, "Mus musculus DEAD (Asp-Glu-Ala-Asp) box polypeptide 58 (Ddx58), mRNA," Jun. 30, 2012, 5 pages.
GenBank® accession NM_172893, "Mus musculus poly (ADP-ribose) polymerase family, member 12 (Parp12), mRNA," Jun. 30, 2012, 4 pages.
GenBank® accession NM_175026, "Mus musculus pyrin and HIN domain family, member 1 (Pyhin1), mRNA," Jun. 30, 2012, 3 pages.
GenBank® accession NM_194336, "Mus musculus guanylate binding protein 6 (Gbp6), mRNA," Jun. 30, 2012, 4 pages.
GenBank® accession NM_198095, "Mus musculus bone marrow stromal cell antigen 2 (Bst2), mRNA," Jun. 29, 2012, 3 pages.
GenBank® accession NM_207648, "Mus musculus histocompatibility 2, Q region locus 6 (H2-Q6), mRNA," Dec. 12, 2012, 3 pages.
GenBank® accession XM_001476651, "Predicted: Mus musculus ring finger protein 213 (Rnf213), mRNA," Sep. 28, 2012, 6 pages.
GenBank® accession XR_104969, "Predicted: Mus musculus predicted gene, 20559 (Gm20559), misc_RNA," Sep. 28, 2012, 2 pages.

\* cited by examiner

| | | | | |
|---|---|---|---|---|
| 1 | ATGGGTGCCA | TCGTAGACAT | TTCCACAGGA | TCTGTTGTGC |
| 41 | ATGTCCCCAG | AAAGACCAAA | TTGAGGAGAA | CAGTCGCTCA |
| 81 | TGATGTTTTC | CAACCCAAAT | TCGAACCTGC | AGTGCTGTCA |
| 121 | CGCTATGACC | CTCGGACTGA | TAAGGACGTT | GATGTTGTAG |
| 161 | CTTTTTCCAA | ACACACCACT | AACATGGAAA | GCTTGCCCCC |
| 201 | GGTCTTTGAT | ATCGTCTGTG | ATGAATACGC | TAACCGCGTC |
| 241 | TTCACTATCC | TTGGTAAAGA | CAACGGTCTT | CTGACCGTTG |
| 281 | AACAGGCCGT | GCTTGGCTTG | CCAGGTATGG | ACCCCATGGA |
| 321 | GAAGGACACC | TCTCCTGGAT | TGCCCTACAC | TCAACAAGGA |
| 361 | CTTAGACGAA | CCGACCTTCT | GGATTTCAAC | ACTGCTAAAA |
| 401 | TGACACCTCA | ATTGGACTAC | GCCCATTCCA | AATTGGTGCT |
| 441 | CGGCGTCTAT | GACGACGTCG | TCTACCAATC | ATTTTTGAAA |
| 481 | GATGAAATTC | GACCCTTGGA | GAAGATCCAC | GAAGCAAAAA |
| 521 | CCCGGATTGT | TGACGTACCC | CCGTTTGCTC | ACTGCATTTG |
| 561 | GGGAAGACAG | CTTCTGGGAC | GTTTTGCCTC | CAAATTCCAG |
| 601 | ACCAAACCCG | GACTCGAACT | CGGATCTGCA | ATTGGAACTG |
| 641 | ACCCGGACGT | TGATTGGACA | CGCTACGCCG | CTGAGCTGAG |
| 681 | TGGGTTCAAT | TACGTCTATG | ATGTAGATTA | CTCCAACTTT |
| 721 | GATGCTTCCC | ATTCTACTGC | AATGTTTGAA | TGCTTGATCA |
| 761 | AGAATTTCTT | CACAGAGCAA | AATGGATTTG | ACAGACGCAT |
| 801 | TGCCGAGTAT | CTCAGATCCT | TGGCTGTGTC | GCGACATGCT |
| 841 | TACGAGGACC | GCCGTGTCCT | TATACGTGGA | GGCTTGCCTT |
| 881 | CGGGCTGCGC | TGCCACCAGC | ATGTTAAACA | CCATCATGAA |
| 921 | CAATGTTATA | ATTCGTGCTG | CCCTGTACCT | TACCTACTCA |
| 961 | AATTTTGAAT | TTGATGATAT | TAAGGTCCTT | TCCTATGGAG |
| 1001 | ATGACCTTTT | AATTGGAACT | AATTACCAAA | TTGATTTCAA |
| 1041 | TCTTGTTAAA | GAAAGATTAG | CCCCCTTCGG | TTATAAGATT |
| 1081 | ACTCCTGCCA | ACAAGACCAC | CACCTTTCCC | CTGACCTCCC |
| 1121 | ATTTGCAAGA | TGTTACCTTT | CTAAAGAGGA | GATTTGTGAG |
| 1161 | ATTCAATTCC | TACCTGTTTA | GACCTCAAAT | GGATGCTGTC |
| 1201 | AACTTGAAAG | CAATGGTTAG | CTACTGTAAA | CCAGGAACAC |
| 1241 | TTAAAGAGAA | ACTAATGTCC | ATTGCTCTTC | TGGCCGTTCA |
| 1281 | CTCCGGACCA | GATATATATG | ATGAGATTTT | CCTGCCCTTT |
| 1321 | AGGAATGTTG | GAATAGTTGT | CCCTACCTAT | AGTTCTATGC |
| 1361 | TTTATAGATG | GCTTAGCTTA | TTTAGACGTG | ATATCACCGG |
| 1401 | TCATCATCAC | CATCACCAT | | |

FIG. 1

```
  1  MGAIVDISTGSVVHVPRKTKLRRTVAHDVFQPKFE
 36  PAVLSRYDPRTDKDVDVVAFSKHTTNMESLPPVFD
 71  IVCDEYANRVFTILGKDNGLLTVEQAVLGLPGMDP
106  MEKDTSPGLPYTQQGLRRTDLLDFNTAKMTPQLDY
141  AHSKLVLGVYDDVVYQSFLKDEIRPLEKIHEAKTR
176  IVDVPPFAHCIWGRQLLGRFASKFQTKPGLELGSA
211  IGTDPDVDWTRYAAELSGFNYVYDVDYSNFDASHS
246  TAMFECLIKNFFTEQNGFDRRIAEYLRSLAVSRHA
281  YEDRRVLIRGGLPSGCAATSMLNTIMNNVIIRAAL
316  YLTYSNFEFDDIKVLSYGDDLLIGTNYQIDFNLVK
351  ERLAPFGYKITPANKTTTFPLTSHLQDVTFLKRRF
386  VRFNSYLFRPQMDAVNLKAMVSYCKPGTLKEKLMS
421  IALLAVHSGPDIYDEIFLPFRNVGIVVPTYSSMLY
456  RWLSLFRRDITGHHHHHH
```

FIG. 2

```
   1 AUGGGUGCCAUCGUAGACAUUUCCACAGGAUCUGUUGUGC
  41 AUGUCCCCAGAAAGACCAAAUUGAGGAGAACAGUCGCUCA
  81 UGAUGUUUCCAACCCAAAUUCGAACCUGCAGUGCUGUCA
 121 CGCUAUGACCCUCGGACUGAUAAGGACGUUGAUGUUGUAG
 161 CUUUUUCCAAACACACCACUAACAUGGAAAGCUUGCCCCC
 201 GGUCUUUGAUAUCGUCUGUGAUGAAUACGCUAACCGCGUC
 241 UUCACUAUCCUUGGUAAAGACAACGGUCUUCUGACCGUUG
 281 AACAGGCCGUGCUUGGCUUGCCAGGUAUGGACCCCAUGGA
 321 GAAGGACACCUCUCCUGGAUUGCCCUACACUCAACAAGGA
 361 CUUAGACGAACCGACCUUCUGGAUUUCAACACUGCUAAAA
 401 UGACACCUCAAUUGGACUACGCCCAUUCCAAAUUGGUGCU
 441 CGGCGUCUAUGACGACGUCGUCUACCAAUCAUUUUGAAA
 481 GAUGAAAUUCGACCCUUGGAGAAGAUCCACGAAGCAAAAA
 521 CCCGGAUUGUUGACGUACCCCGUUUGCUCACUGCAUUUG
 561 GGGAAGACAGCUUCUGGGACGUUUGCCUCCAAAUUCCAG
 601 ACCAAACCCGGACUCGAACUCGGAUCUGCAAUUGGAACUG
 641 ACCCGGACGUUGAUUGGACACGCUACGCCGCUGAGCUGAG
 681 UGGGUUCAAUUACGUCUAUGAUGUAGAUUACUCCAACUUU
 721 GAUGCUUCCCAUUCUACUGCAAUGUUUGAAUGCUUGAUCA
 761 AGAAUUUCUUCACAGAGCAAAAUGGAUUUGACAGACGCAU
 801 UGCCGAGUAUCUCAGAUCCUUGGCUGUGUCGCGACAUGCU
 841 UACGAGGACCGCCGUGUCCUAUACGUGGAGGCUUGCCUU
 881 CGGGCUGCGCUGCCACCAGCAUGUUAAACACCAUCAUGAA
 921 CAAUGUUAUAAUUCGUGCUGCCCUGUACCUUACCUACUCA
 961 AAUUUUGAAUUUGAUGAUAUUAAGGUCCUUUCCUAUGGAG
1001 AUGACCUUUUAAUUGGAACUAAUUACCAAAUUGAUUUCAA
1041 UCUUGUUAAGAAAGAUUAGCCCCCUUCGGUUAUAAGAUU
1081 ACUCCUGCCAACAAGACCACCACCUUUCCCCUGACCUCCC
1121 AUUUGCAAGAUGUUACCUUCUAAAGAGGAGAUUUGUGAG
1161 AUUCAAUUCCUACCUGUUUAGACCUCAAAUGGAUGCUGUC
1201 AACUUGAAAGCAAUGGUUAGCUACUGUAAACCAGGAACAC
1241 UUAAAGAGAAACUAAUGUCCAUUGCUCUUCGGCCGUUCA
1281 CUCCGGACCAGAUAUAUGAUGAGAUUUCCUGCCCUUU
1321 AGGAAUGUUGGAAUAGUUGUCCCUACCUAUAGUUCUAUGC
1361 UUUAUAGAUGGCUUAGCUUAUUUAGACGUGAUAUCACCGG
1401 UCAUCAUCACCAUCACCAU
```

FIG. 3 codon optimized, scrambled design

US 9,421,242 B2

METHODS AND MATERIALS FOR REDUCING THE SEVERITY OF VIRAL INFECTIONS

BACKGROUND

1. Technical Field

This document relates to methods and materials involved in reducing viral infection severity and/or treating a viral infection (e.g., a picornavirus infection or a non-picornavirus infection such as a herpesvirus infection) present in a mammal. For example, this document provides methods and materials for reducing the severity of a non-picornavirus viral infection present in a mammal (e.g., a human). In addition, this document provides methods and materials for enhancing innate immunity within a mammal by increasing the expression levels of a set of nucleic acids that encode polypeptides involved in innate immunity.

2. Background Information

Viral infections such as picornavirus infections are a major contributor to world-wide disease. Diseases such as poliomyelitis and hand-foot-and-mouth disease can be fatal to humans and other mammals and animals. Other picornaviruses, such as the rhinovirus, are partly responsible for upper respiratory tract infections.

Picornaviruses perform multiple tasks inside host cells for successful viral replication with very few gene products responsible for these tasks. The single-stranded RNA picornavirus genome has, on average, about 7500 nucleotides and produces a single polyprotein that is cleaved by its own virally encoded proteases. One of these proteins, the RNA-dependent RNA-polymerase, 3Dpol, is required for elongation of positive and negative stranded viral RNA. 3Dpol oligomerizes, which favors elongation and binding to RNA. 3Dpol forms a membranous replication complex with VPg and precursor proteins 3AB and 3CD to initiate VPg uridylylation, which serves as a primer for positive and negative RNA strand replication by 3Dpol.

SUMMARY

This document provides methods and materials involved in reducing viral infection severity and/or treating a viral infection (e.g., a picornavirus infection or a non-picornavirus infection such as a herpesvirus infection) present in a mammal. For example, this document provides methods and materials for reducing the severity of a picornavirus infection (e.g., foot-and-mouth or hoof-and-mouth disease) or a herpesvirus infection (e.g., a pseudorabies virus infection) present in a mammal (e.g., a human). In addition, this document provides methods and materials for enhancing innate immunity within a mammal by increasing the expression levels of a set of nucleic acids that encode polypeptides involved in innate immunity. For example, this document provides methods and materials for delivering RNA (e.g., single-stranded or double-stranded RNA) encoding a picornavirus 3Dpol polypeptide, RNA (e.g., single-stranded or double-stranded RNA) encoding a fragment of a picornavirus 3Dpol polypeptide, one or more nucleic acid molecules designed to express RNA (e.g., single-stranded or double-stranded RNA) encoding a picornavirus 3Dpol polypeptide, or one or more nucleic acid molecules designed to express RNA (e.g., single-stranded or double-stranded RNA) encoding a fragment of a picornavirus 3Dpol polypeptide under conditions wherein the level of expression of a set of nucleic acids that encode polypeptides involved in innate immunity is increased. In some cases, this document provides methods and materials for delivering a picornavirus 3Dpol polypeptide or a fragment of a picornavirus 3Dpol polypeptide (e.g., a fragment of a picornavirus 3Dpol polypeptide that is between about 100 and 550 amino acids in length) to a mammal (e.g., a human) under conditions wherein innate immunity within the mammal is increases and/or the level of expression of a set of nucleic acids that encode polypeptides involved in innate immunity is increased.

In general, one aspect of this document features a method for increasing expression of a set of nucleic acids encoding polypeptides involved in innate immunity within a mammal. The method comprises, or consists essentially of, administering a viral vector (e.g., a lentiviral vector) comprising nucleic acid encoding a picornavirus 3Dpol polypeptide or a fragment thereof to the mammal under conditions wherein the expression of the set of nucleic acids is increased, wherein the polypeptides involved in innate immunity include two or more (e.g., 2, 3, 4, 5, or 6) of the following polypeptides: an Oas gene family polypeptide, an Ifit gene family polypeptide, an Isg15 polypeptide, a Rig-1 polypeptide, a Mda5 polypeptide, and a Mx1 polypeptide. The mammal can be a human. The picornavirus 3Dpol polypeptide can comprise the amino acid sequence set forth in SEQ ID NO:2. The administering can comprise an oral administration. The administering can comprise an intravenous administration. The administering can comprise a nasal inhalation. The viral vector (e.g., lentiviral vector) can comprise nucleic acid encoding a fragment of the picornavirus 3Dpol polypeptide that is between 100 and 550 (e.g., between 100 and 470, between 100 and 500, or between 100 and 475) amino acid residues in length. In some cases, a tag sequence (e.g., a his tag) can be attached to the fragment.

In another aspect, this document features a method for increasing expression of a set of nucleic acids encoding polypeptides involved in innate immunity within a mammal. The method comprises, or consists essentially of, administering a composition comprising RNA encoding a picornavirus 3Dpol polypeptide or a fragment thereof to the mammal under conditions wherein the expression of the set of nucleic acids is increased, wherein the polypeptides involved in innate immunity include two or more (e.g., 2, 3, 4, 5, or 6) of the following polypeptides: an Oas gene family polypeptide, an Ifit gene family polypeptide, an Isg15 polypeptide, a Rig-1 polypeptide, a Mda5 polypeptide, and a Mx1 polypeptide. The mammal can be a human. The picornavirus 3Dpol polypeptide can comprise the amino acid sequence set forth in SEQ ID NO:2. The administering can comprise an intravenous administration. The administering can comprise a nasal inhalation. The RNA can encode a fragment of the picornavirus 3Dpol polypeptide that is between 100 and 550 (e.g., between 100 and 470, between 100 and 500, or between 100 and 475) amino acid residues in length. In some cases, a tag sequence (e.g., a his tag) can be attached to the fragment.

In another aspect, this document features a method for increasing expression of a set of nucleic acids encoding polypeptides involved in innate immunity within a mammal. The method comprises administering a RNA-dependent RNA-polymerase (3Dpol) polypeptide or a catalytically active fragment thereof or nucleic acid encoding the 3Dpol polypeptide or the catalytically active fragment thereof to the mammal under conditions wherein the expression of the set of nucleic acids is increased, wherein the polypeptides involved in innate immunity comprise an Oas gene family polypeptide, an Ifit gene family polypeptide, an Isg15 polypeptide, a Rig-1 polypeptide, a Mda5 polypeptide, and a Mx1 polypeptide. The method can comprise administering the nucleic acid to the mammal. The 3Dpol polypeptide or the fragment can be expressed within cells of the mammal. The method can comprise administering the polypeptide or fragment to the mammal. The mammal can be a human. The picornavirus 3Dpol polypeptide can comprise the amino acid sequence set forth in SEQ ID NO:2. The administering can comprise an oral administration. The administering can comprise administering a lentiviral vector comprising the nucleic acid. The administering can comprise an intravenous administration or a nasal inhalation. The method comprises administering the fragment or nucleic acid encoding the fragment, and wherein the fragment can be between 100 and 550 (e.g., between 100 and 470, between 100 and 500, or between 100 and 475) amino acid residues in length. In some cases, a tag sequence (e.g., a his tag) can be attached to the fragment.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is a sequence listing of nucleic acid (SEQ ID NO:1) that encodes a picornavirus 3Dpol polypeptide. See, also, GenBank® accession #M20301 nucleotides 6586-7968.

FIG. 2 is a sequence listing of an amino acid sequence (SEQ ID NO:2) of a picornavirus 3Dpol polypeptide. SEQ ID NO:2 is an amino acid sequence that can be encoded by the nucleic acid sequence set forth in SEQ ID NO:1.

FIG. 3 is a sequence listing of an RNA molecule (SEQ ID NO:3) that can be transcribed from a nucleic acid encoding a picornavirus 3Dpol polypeptide. SEQ ID NO:3 is an RNA sequence that can be transcribed from the nucleic acid sequence set forth in SEQ ID NO:1.

FIG. 4 contains graphs plotting expression levels for the prominent antiviral response genes, Oas12, Ifit1, Isg15, Ifit3, Oas1a, Tetherin (Bst2), Viperin (Rsad2), Rig-1, Ifit2, Ifitm3, and Mx1 in wild-type FVB mice infected with EMCV (WT +EMCV), uninfected 3Dpol mice (3D), and 3Dpol mice infected with EMCV (3D +EMCV). *$p<0.05$, $p<0.01$, *$p<0.001$, #$p<0.0001$, ##$p<1.0$ E-5, ###$p<1.0$ E-6. Error bars represent±SEM.

FIG. 5 contains graphs plotting expression levels of Oas12, Isg15, Ifit1, and Rig-1 in the indicated tissue from either uninfected, wild-type FVB mice (WT) or uninfected 3Dpol mice (3D). RT-PCR was used to determine expression levels of these prominent antiviral response genes in tissues of uninfected WT (n=3) and uninfected 3D mice (n=3). Data are expressed as the ratio of induced transcript normalized to endogenous GAPDH (±SEM). *$p<0.05$; $p<0.01$; *$p<0.001$, ****$p<0.0001$ (Student's two-tailed unpaired t test).

FIG. 6 contains photographs of Western blot analyses of dermal fibroblast cell lysates, or cerebral, spinal cord, and cerebellar tissue homogenates from uninfected wild-type FVB mice (WT) or uninfected 3Dpol mice (3D) (n=2 mice per genotype, 1 mouse per lane). Samples were analyzed using antibodies for the antiviral effectors RIG-1 and ISG15. Antibodies against β-actin were used as control.

FIG. 7. Innate antiviral gene induction in 3Dpol mice is dependent on MDA5 and type I interferon (IFN) signaling, independent of IFN gamma signaling, and independent of adaptive immune signaling. Cerebral, spinal cord, and cerebellar tissue homogenates of transgenic mice were analyzed by Western blot analysis using antibodies for RIG-1 and ISG15. Antibodies against β-actin were used as control. A, Type I IFN deficient mice (Ifnar1$^{-/-}$) or 3D-Ifnar1$^{-/-}$ mice (n=2 mice per genotype, 1 mouse per lane). B, IFN gamma (Ifngr1$^{-/-}$) or 3D-Ifngr1$^{-/-}$ mice (n=2 mice per genotype, 1 mouse per lane). C, Rag1 (Rag1$^{-/-}$) deficient mice devoid of mature T and B cells or 3D-Rag1$^{-/-}$ mice (n=2 mice per genotype, 1 mouse per lane). D, MDA5$^{-/-}$ mice or 3D-MDA5$^{-/-}$ mice (n=2 mice per genotype, 1 mouse per lane).

FIG. 8. A, Schematic diagram of the lentiviral vectors used to express nucleic acid encoding a catalytically-active picornavirus 3Dpol polypeptide, nucleic acid encoding a picornavirus 3Dpol polypeptide lacking the active site of the polymerase, or codon optimized nucleic acid encoding a picornavirus 3Dpol polypeptide lacking secondary transcript structure. B, Heat map showing the differentially expressed genes in THP-1 cells; THP-1 cells expressing a catalytically-active picornavirus 3Dpol polypeptide (3D THP-1 cells), THP-1 cells expressing a catalytically-inactive picornavirus 3Dpol polypeptide (ΔAct 3D THP-1 cells), or THP-1 cells expressing a catalytically-active picornavirus 3Dpol polypeptide expressed from codon-optimized nucleic acid (codon 3D THP-1 cells).

DETAILED DESCRIPTION

This document provides methods and materials involved in reducing viral infection severity and/or treating a viral infection (e.g., a picornavirus infection or a non-picornavirus infection such as a herpesvirus infection) present in a mammal. For example, this document provides methods and materials for reducing the severity of a picornavirus infection (e.g., foot-and-mouth or hoof-and-mouth disease) or a herpesvirus infection (e.g., a pseudorabies virus infection) present in a mammal (e.g., a human). In addition, this document provides methods and materials for enhancing innate immunity within a mammal by increasing the expression levels of a set of nucleic acids that encode polypeptides involved in innate immunity. For example, this document provides methods and materials for delivering RNA (e.g., single-stranded or double-stranded RNA) encoding a picornavirus 3Dpol polypeptide, RNA (e.g., single-stranded or double-stranded RNA) encoding a fragment of a picornavirus 3Dpol polypeptide, one or more nucleic acid molecules designed to express RNA (e.g., single-stranded or double-stranded RNA) encoding a picornavirus 3Dpol polypeptide, or one or more nucleic acid molecules designed to express RNA (e.g., single-stranded or double-stranded RNA) encoding a fragment of a picornavirus 3Dpol polypeptide under conditions wherein the level of expression of a set of nucleic acids that encode polypeptides involved in innate immunity is increased. In some cases, this document provides methods and materials for delivering a picornavirus 3Dpol polypeptide or a fragment of a picornavirus 3Dpol polypeptide (e.g., a fragment of a picornavirus 3Dpol polypeptide that is between about 100 and 550 amino acids in length) to a mammal (e.g., a human) under conditions wherein innate immunity within the mammal is increases and/or the level of expression of a set of nucleic acids that encode polypeptides involved in innate immunity is increased.

Figure 4:
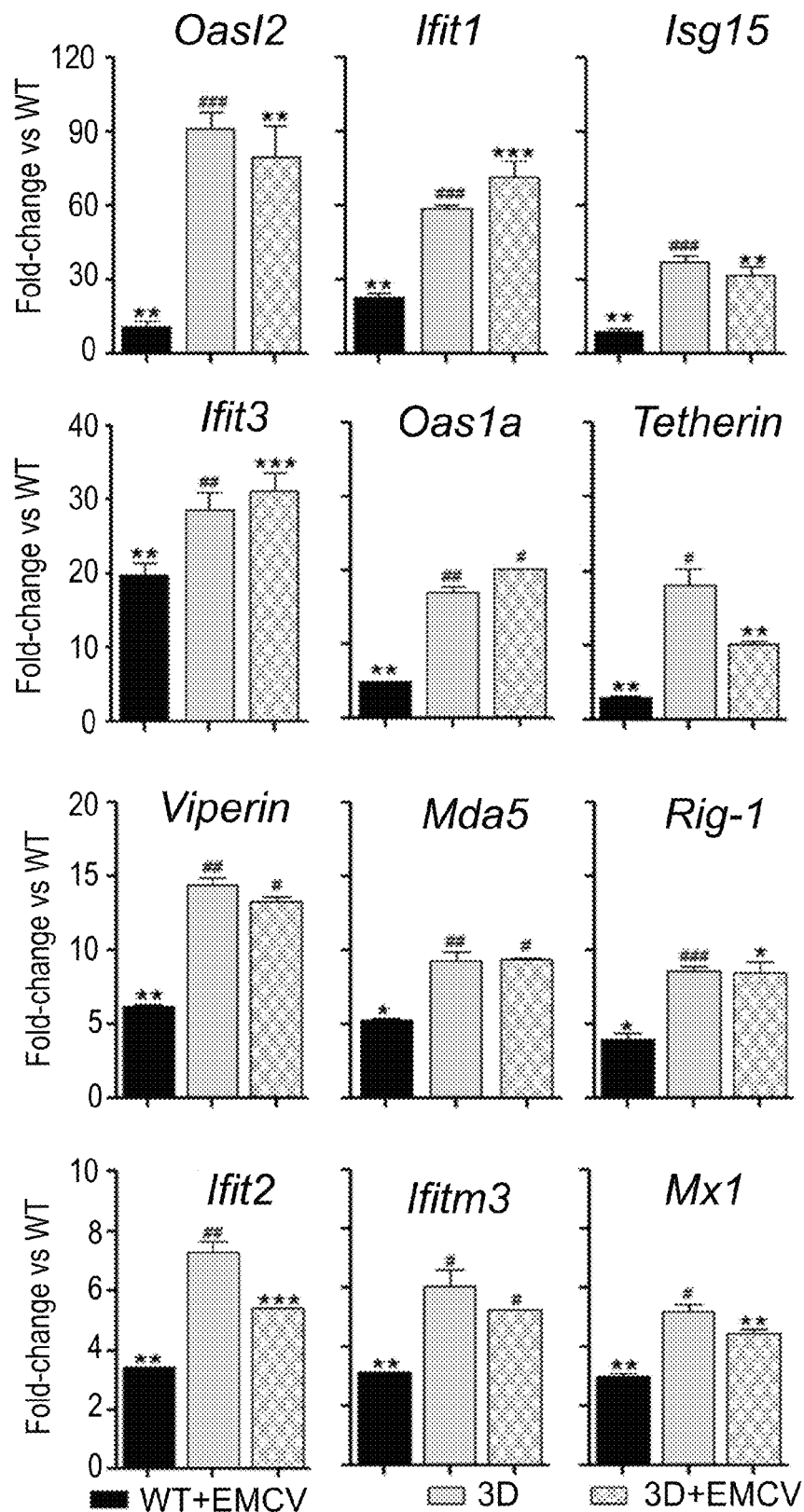
Figure 5:
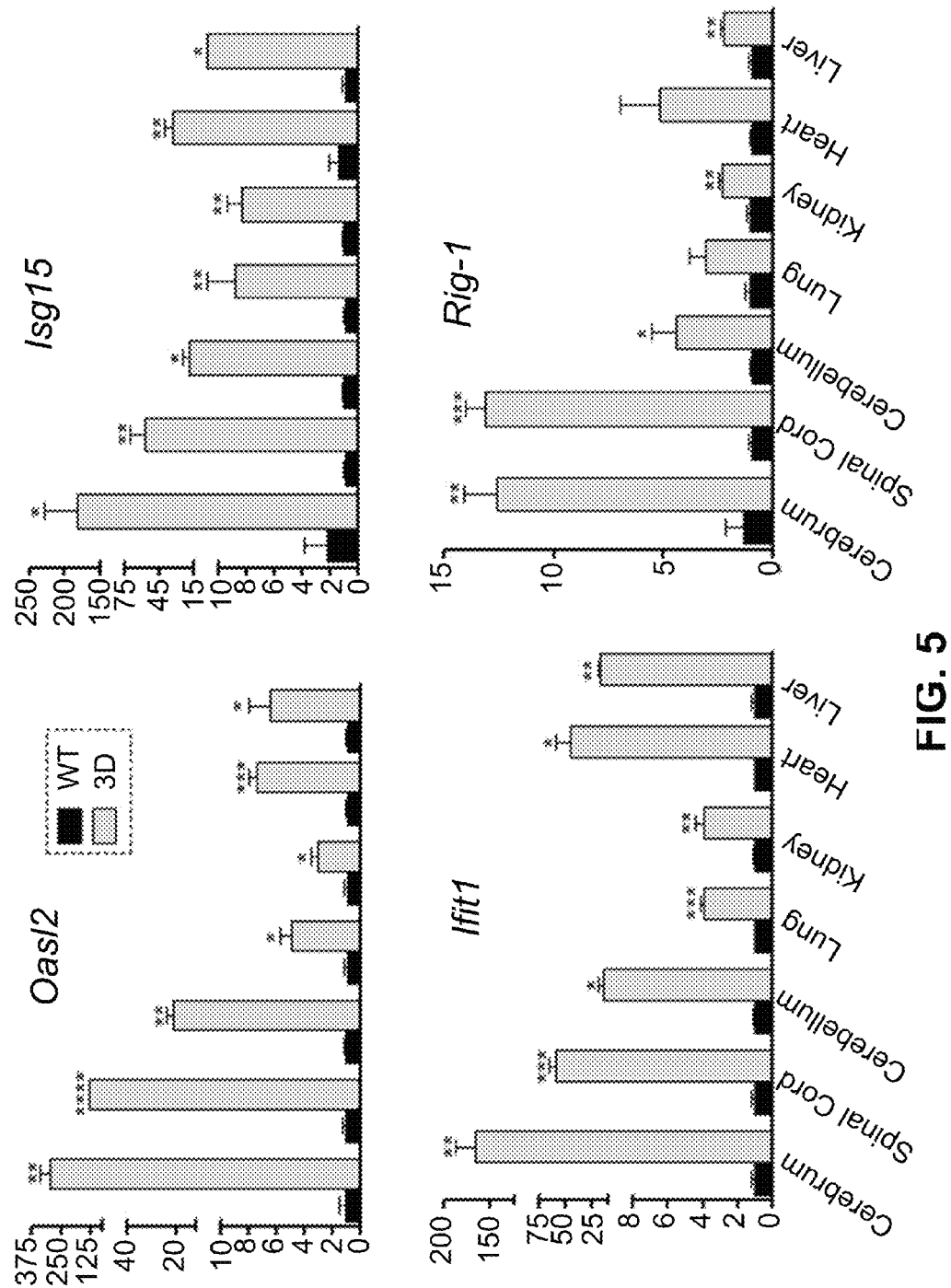
Figure 6:
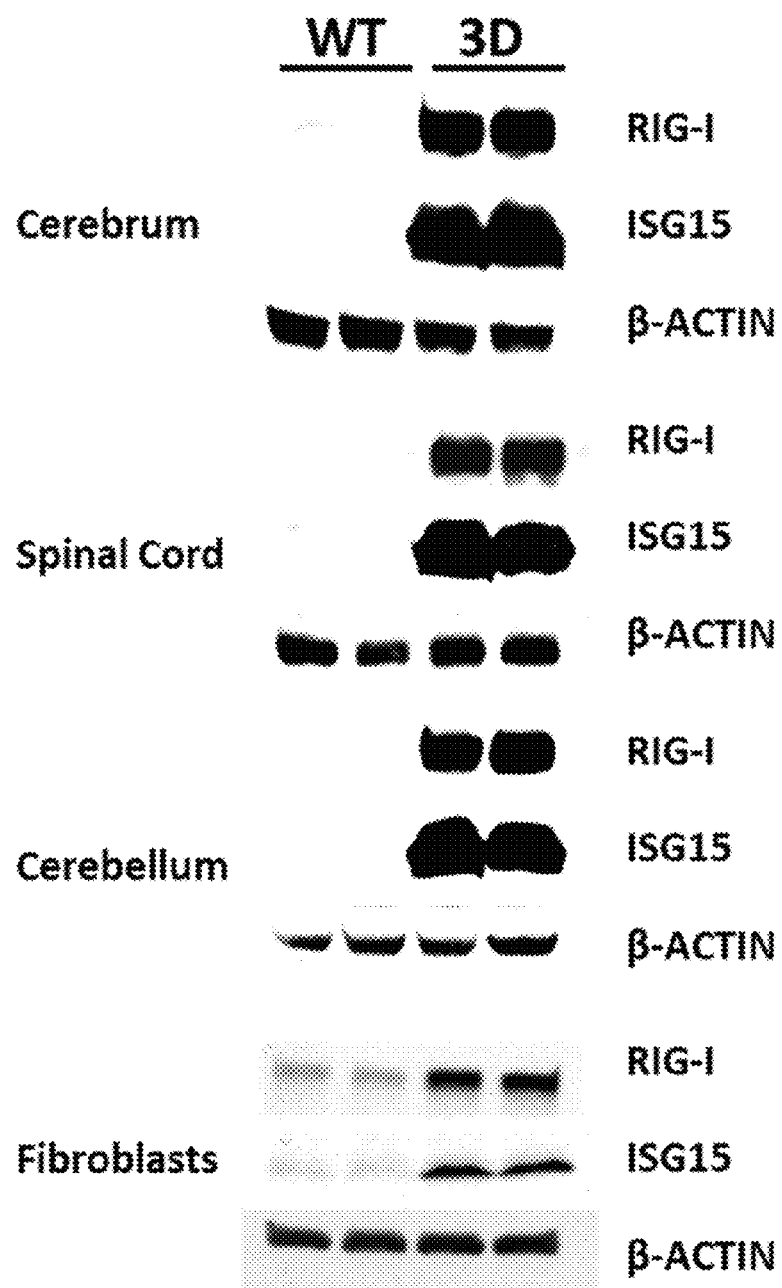
Figure 7:
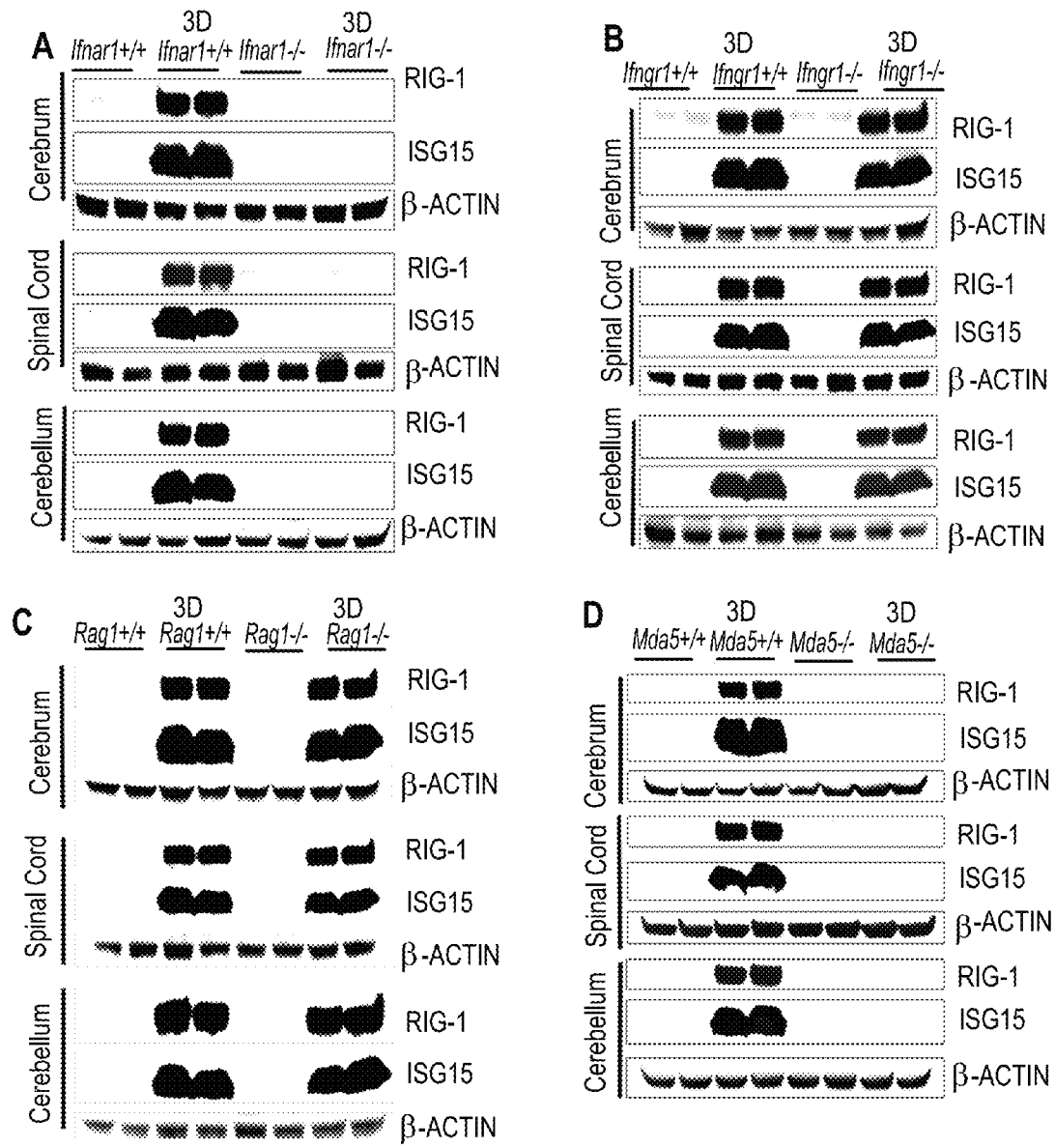

In some cases, a fragment of the picornavirus 3Dpol polypeptide can be between about 100 and about 550 amino acid residues in length (e.g., between about 100 and about 500 amino acid residues in length, between about 100 and about 475 amino acid residues in length, between about 200 and about 550 amino acid residues in length, between about 250 and about 550 amino acid residues in length, between about 300 and about 550 amino acid residues in length, between about 350 and about 500 amino acid residues in length, between about 400 and about 500 amino acid residues in length, or between about 100 and about 470 amino acid residues in length).

As described herein, a mammal having a viral infection (e.g., a picornavirus infection or a non-picornavirus infection such as a herpesvirus infection) can be treated by administering a picornavirus 3Dpol polypeptide or nucleic acid (e.g., DNA, RNA, or a combination thereof) encoding a picornavirus 3Dpol polypeptide. In some cases, such nucleic acid can be administered such that RNA encoding a picornavirus 3Dpol polypeptide and/or a picornavirus 3Dpol polypeptide is expressed. In some cases, a fragment of a picornavirus 3Dpol polypeptide or a nucleic acid (e.g., DNA, RNA, or a combination thereof) encoding a fragment of a picornavirus 3Dpol polypeptide can be used as described herein. For example, a fragment of a picornavirus 3Dpol polypeptide that includes 30, 40, 50, 60, 70, 80, 85, 90, 95, 99, or 100 percent of the amino acid residues set forth in SEQ ID NO:2 can be used as described herein. In some cases, a nucleic acid that encodes 30, 40, 50, 60, 70, 80, 85, 90, 95, 99, or 100 percent of the amino acid residues set forth in SEQ ID NO:2 can be used as described herein.

Administration of a picornavirus 3Dpol polypeptide or a fragment of a picornavirus 3Dpol polypeptide can result in increased expression of a set of nucleic acids that encode polypeptides involved in innate immunity and/or a reduced viral load and/or a reduced virus-induced pathology (e.g., reduced picornavirus-induced brain and spinal cord pathology). In some cases, the presence of the nucleic acid, the expression of RNA encoding a picornavirus 3Dpol polypeptide (or fragment thereof), the expression of a picornavirus 3Dpol polypeptide (or fragment thereof), or all three can result in increased expression of a set of nucleic acids that encode polypeptides involved in innate immunity and/or a reduced viral load and/or a reduced virus-induced pathology (e.g., reduced picornavirus-induced brain and spinal cord pathology). In some cases, a picornavirus 3Dpol polypeptide (or a fragment thereof) or RNA encoding a picornavirus 3Dpol polypeptide (or a fragment thereof) can be administered to a mammal to reduce the severity of a current or future viral infection and/or to treat a viral infection. For example, RNA encoding a picornavirus 3Dpol polypeptide (or a fragment thereof) can be administered to a mammal under conditions that reduce the severity of a viral infection (e.g., a picornavirus infection or a non-picornavirus infection such as herpesvirus infection) present in the mammal (e.g., a human). In some cases, the administration of RNA encoding a picornavirus 3Dpol polypeptide (or a fragment thereof) can result in reduced viral load (e.g., reduced picornavirus or a non-picornavirus infection such as herpesvirus virus load) and/or reduced virus-induced pathology (e.g., reduced picornavirus-induced brain and spinal cord pathology).

Examples of non-picornavirus viral infections that can be treated as described herein include, without limitation, herpesvirus infections, retrovirus infections, orthomyxovirus infections, filovirus infections, flavivirus infections, and hepadnavirus infections.

Examples of nucleic acids that encode polypeptides involved in innate immunity that can undergo increased levels of expression within a mammal following administration of nucleic acid (e.g., DNA, RNA, or a combination thereof) encoding a picornavirus 3Dpol polypeptide (or a fragment thereof) are set forth in Table 1.

TABLE 1

List of nucleic acids that encode polypeptides involved in innate immunity.

| Gene Name | GenBank ® Accession Number (Mouse) | GenBank ® Accession Number (Human) |
|---|---|---|
| Oas1 | (Oas1a) NM_145211 | NM_016816 |
| Oas2 | NM_145227 | NM_001032731 |
| Oas3 | NM_145226 | NM_006187 |
| Oasl | (Oasl2) NM_011854 | NM_003733 |
| Ifit1 | NM_008331 | NM_001548 |
| Ifit2 | NM_008332 | NM_001547 |
| Ifit3 | NM_010501 | NM_001549 |
| Ifitm3 | NM_025378 | NM_021034 |
| Rig-1 (Ddx58) | NM_172689 | NM_014314 |
| Mda5 (Ifih1) | NM_001164477 | NM_022168 |
| Pkr (Eif2ak2) | NM_011163 | NM_002759 |
| Mx1 | NM_010846 | NM_001144925 |
| Mx2 | NM_013606 | NM_002463 |
| Tetherin (Bst2) | NM_198095 | NM_004335 |
| Viperin (Rsad2) | NM_021384 | NM_080657 |
| ZAP (Zc3hav1) | NM_028421 | NM_020119 |
| Isg15 | NM_015783 | NM_005101 |

Any appropriate mammal can be treated as described herein including, without limitation, humans, cows, pigs, sheep, horses, goats, llamas, elk, deer, bison, dogs, and cats. Any appropriate method can be used to identify a mammal having a viral infection (e.g., a picornavirus or herpesvirus infection) or at risk of being virally infected. For example, PCR-based assays such as those that quantify viral transcripts, e.g., in the tissue, saliva, or stool as is appropriate for the specific virus by real-time quantitative PCR, or a serological assay that quantifies viral specific IgM or IgG can be used to identify a mammal having a viral infection. Once identified, a mammal having a viral infection or at risk of a viral infection can be treated by administering DNA encoding a picornavirus 3Dpol polypeptide to the mammal, by administering RNA encoding a picornavirus 3Dpol polypeptide to the mammal, or by administering both DNA encoding a picornavirus 3Dpol polypeptide and RNA encoding a picornavirus 3Dpol polypeptide to the mammal. In some cases, such administrations can be performed under conditions that increase the level of a picornavirus 3Dpol polypeptide in the mammal. In some cases, a mammal having a viral infection or at risk of a viral infection can be treated by administering a picornavirus 3Dpol polypeptide (or a fragment thereof) to the mammal.

A nucleic acid described herein can encode a picornavirus 3Dpol polypeptide having the amino acid sequence set forth in SEQ ID NO:2. Additional examples of nucleic acids that encode a picornavirus 3Dpol polypeptide include, without limitation, those set forth in GenBank® having accession numbers NC_001366 (nucleotides 6594-7976; GI No: 9626123), NC_009448 (nucleotides 6546-7928; GI No: 182406744), NC_001479 (nucleotides 6330-7707; GI No: 9626692), NC_003982 (nucleotides 6233-7624; GI No: 21328570), NC_004004 (nucleotides 6615-8024; GI No: 21426907), and NC_002058 (nucleotides 5987-7369; GI No: 12408699).

A nucleic acid encoding a picornavirus 3Dpol polypeptide can be administered to a mammal using a vector. For example, a nucleic acid can be administered to a mammal using a vector such as a viral vector. In some cases, a nucleic acid encoding a picornavirus 3Dpol polypeptide (or a fragment thereof) can include sequences that direct replication of the nucleic acid. Vectors for administering nucleic acids (e.g., a nucleic acid encoding a picornavirus 3Dpol polypeptide) to a mammal can be prepared using standard materials (e.g., packaging cell lines, helper viruses, and vector constructs). See, for example, *Gene Therapy Protocols* (*Methods in Molecular Medicine*), edited by Jeffrey R. Morgan, Humana Press, Totowa, N.J. (2002) and *Viral Vectors for Gene Therapy: Methods and Protocols*, edited by Curtis A. Machida, Humana Press, Totowa, N.J. (2003). Virus-based nucleic acid delivery vectors can be derived from animal viruses, such as adenoviruses, adeno-associated viruses, retroviruses, lentiviruses, vaccinia viruses, herpes viruses, and papilloma viruses. Vectors for nucleic acid delivery can be genetically modified such that the pathogenicity of the virus is altered or removed. The genome of a virus can be modified to increase infectivity and/or to accommodate packaging of a nucleic acid, such as a nucleic acid encoding a picornavirus 3Dpol polypeptide. A viral vector can be replication-competent or replication-defective, and can contain fewer viral genes than a corresponding wild-type virus or no viral genes at all.

In some cases, a lentiviral vector can be designed to express RNA encoding a picornavirus 3Dpol polypeptide. Such a lentiviral vector can be administered to a mammal as described herein to induce expression of a set of nucleic acids that encode polypeptides involved in innate immunity.

In addition to nucleic acid encoding a picornavirus 3Dpol polypeptide, a viral vector (e.g., a lentiviral vector) can contain regulatory elements operably linked to a nucleic acid encoding a picornavirus 3Dpol polypeptide. Such regulatory elements can include promoter sequences, enhancer sequences, response elements, signal peptides, internal ribosome entry sequences, polyadenylation signals, terminators, or inducible elements that modulate expression (e.g., transcription or translation) of a nucleic acid. The choice of element(s) that may be included in a viral vector depends on several factors, including, without limitation, inducibility, targeting, and the level of expression desired. For example, a promoter can be included in a viral vector to facilitate transcription of a nucleic acid encoding a picornavirus 3Dpol polypeptide. A promoter can be constitutive or inducible (e.g., in the presence of tetracycline), and can affect the expression of a nucleic acid encoding a picornavirus 3Dpol polypeptide in a general or tissue-specific manner. General promoters can include, without limitation, cytomegalovirus (CMV) promoters and ubiquitin promoters. Tissue-specific promoters can include, without limitation, neuron specific enolase promoters for neurons, glial fibrillary acidic protein (GFAP) promoters for astrocytes, and myelin basic protein (MBP) promoters for oligodendrocytes.

In some cases, a liver-specific promoter (e.g., a Lap/Cebpb promoter) can be used to direct transcription of RNA encoding a picornavirus 3Dpol polypeptide in liver tissue to treat infections with hepatotropic viruses (e.g., hepatitis C viral infections). In some cases, a heart-specific promoter (e.g., a Myh6 promoter) can be used to direct transcription of RNA encoding a picornavirus 3Dpol polypeptide in heart tissue to treat infections with cardiomyotropic viruses (e.g., Coxsackie B viral infections).

As used herein, "operably linked" refers to positioning of a regulatory element in a vector relative to a nucleic acid in such a way as to permit or facilitate RNA transcription or expression of an encoded polypeptide. For example, a viral vector can contain an oligodendrocyte-specific MBP promoter and a nucleic acid encoding a picornavirus 3Dpol polypeptide. In this case, the MBP promoter is operably linked to a nucleic acid encoding a picornavirus 3Dpol polypeptide such that it drives transcription in oligodendrocytes of the central nervous system.

In some cases, a nucleic acid encoding a picornavirus 3Dpol polypeptide can be administered to a mammal using non-viral vectors. See, for example, *Gene Therapy Protocols* (*Methods in Molecular Medicine*), edited by Jeffrey R. Morgan, Humana Press, Totowa, N.J. (2002). For example, a nucleic acid encoding a picornavirus 3Dpol polypeptide can be administered to a mammal by direct injection of nucleic acid molecules (e.g., plasmids) including nucleic acid encoding a picornavirus 3Dpol polypeptide, or by administering nucleic acid molecules complexed with lipids, polymers, or nanospheres.

A nucleic acid encoding a picornavirus 3Dpol polypeptide can be produced by standard techniques, including, without limitation, common molecular cloning, polymerase chain reaction (PCR), chemical nucleic acid synthesis techniques, and combinations of such techniques. For example, PCR or RT-PCR can be used with oligonucleotide primers designed to amplify viral nucleic acid encoding a picornavirus 3Dpol polypeptide. Once isolated, the nucleic acid can be used to generate a viral vector, for example, which can be administered to a mammal. In some cases, the administered viral vector can result in an increased level of a picornavirus 3Dpol polypeptide in the mammal.

A substantially pure preparation of picornavirus 3Dpol polypeptide (or a fragment thereof) can be produced by standard recombinant polypeptide expression techniques. For example, recombinant polypeptide-producing cell lines and recombinant polypeptide purification techniques can be used. In some cases, cell lines (e.g., bacteria or mammalian cell lines) can be produced to express and amplify viral nucleic acid encoding a picornavirus 3Dpol polypeptide. 3Dpol polypeptides can be designed to express sequences (e.g., tags) that facilitate purification of recombinant 3Dpol polypeptides. Examples of tags include, without limitation, histidine (His), human influenza hemagglutinin (HA), chitin binding protein (CBP), maltose binding protein (MBP), or glutathione-S-transferase (GST) tags. 3Dpol polypeptides expressing sequence tags can be purified from crude cellular sources (e.g., a producer cell line) using standard techniques such as affinity chromatography. Once purified, the 3Dpol polypeptide can be administered to a mammal using any appropriate method, for example, complexed with lipids, polymers, or nanospheres.

Nucleic acid (encoding a picornavirus 3Dpol polypeptide (e.g., a recombinant viral vector)) or 3Dpol polypeptide (or fragment thereof) can be administered to a mammal using any appropriate method, for example, complexed with lipids, polymers, or nanospheres. To circumvent problems associated with cell penetration and cellular targeting, particle targeting techniques can be used. For example, linking a lipid, polymer, or nanosphere to ligands that bind cell surface receptors can be used. In some cases, 3Dpol polypeptide or nucleic acid encoding a picornavirus 3Dpol polypeptide can be complexed with a lipid, polymer, or nanosphere that targets a cognate receptor on mammalian cells and enters via cellular endocytosis, or similar process. Nucleic acid encoding a picornavirus 3Dpol polypeptide (e.g., a recombinant viral vector)) or a 3Dpol polypeptide (or a fragment thereof) can be administered to a mammal using any appropriate method. For example, a 3Dpol polypeptide or a nucleic acid encoding a picornavirus 3Dpol polypeptide can be administered orally, nasally, or by injection (e.g., intravenously).

A composition including a picornavirus 3Dpol polypeptide (or a fragment thereof) or a nucleic acid (e.g., DNA, RNA, or a combination thereof) encoding a picornavirus 3Dpol polypeptide (or a fragment thereof) (e.g., a viral vector) can be in liquid form (e.g., solutions, solvents, suspensions, and emulsions) and can include sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Nucleic acids can be prepared in solid (e.g., lyophilized) form for administration following addition of any appropriate diluent, such as a saline diluent (e.g., 0.4% or 0.9% sodium chloride, pH 7.4).

Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose), fillers (e.g., lactose, microcrystalline cellulose or calcium hydrogen phosphate), lubricants (e.g., magnesium stearate, talc or silica), disintegrants (e.g., potato starch or sodium starch glycolate), or wetting agents (e.g., sodium lauryl sulfate). Tablets can be coated by methods known in the art. Preparations for oral administration can also be formulated to give controlled release of the nucleic acid encoding a picornavirus 3Dpol polypeptide.

Intranasal preparations can be presented in a liquid form (e.g., nasal drops or aerosols) or as a dry product (e.g., a powder). Both liquid and dry nasal preparations can be administered using a suitable inhalation device. Nebulized aqueous suspensions or solutions can also be prepared with or without a suitable pH and/or tonicity adjustment.

A picornavirus 3Dpol polypeptide (or fragment thereof) or a nucleic acid encoding a picornavirus 3Dpol polypeptide (or fragment thereof) can be administered to a mammal such as a human in any amount, at any frequency, and for any duration effective to achieve a desired outcome (e.g., to reduce a symptom of a picornavirus or a non-picornavirus such as a herpesvirus infection). In some cases, a picornavirus 3Dpol polypeptide (or fragment thereof) or nucleic acid encoding a picornavirus 3Dpol polypeptide (or fragment thereof) can be administered to a mammal to reduce a symptom of a picornavirus or herpesvirus infection by 5, 10, 25, 50, 75, 100, or more percent. Any appropriate method can be used to determine whether or not a symptom of a viral infection is reduced. For example, a motor function test, or walking ability, can be used for poliomyelitis or observation of appetite and weight increase as well as decreased malaise and sores can be used for foot and mouth disease. In some cases, a picornavirus 3Dpol polypeptide or a nucleic acid encoding a picornavirus 3Dpol polypeptide can be administered to a mammal to reduce the severity or to delay the onset of a severe viral infection (e.g., a severe picornavirus infection).

An effective amount of a picornavirus 3Dpol polypeptide (or fragment thereof) or a nucleic acid encoding a picornavirus 3Dpol polypeptide (or fragment thereof) can be any amount that reduces a symptom of a viral infection (e.g., a picornavirus or herpesvirus infection) without producing significant toxicity to a mammal. In some cases, the effective amount of nucleic acid encoding a picornavirus 3Dpol polypeptide can be between 0.1 µg/kg and 750 µg/kg (e.g., between 1 µg/kg and 500 µg/kg, between 10 µg/kg and 500 µg/kg, between 100 µg/kg and 500 µg/kg, between 1 µg/kg and 250 µg/kg, between 1 µg/kg and 100 µg/kg, between 10 µg/kg and 400 µg/kg, between 10 µg/kg and 250 µg/kg). In some cases, an effective amount of a nucleic acid encoding a picornavirus 3Dpol polypeptide can be from about $10^3$ to $10^{12}$ (e.g., about $10^8$) recombinant viral particles or plaque forming units (pfu) containing the nucleic acid. If a particular mammal fails to respond to a particular amount, then the amount can be increased by, for example, ten fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment (e.g., the mammal's level of picornavirus 3Dpol RNA or polypeptides or the mammal's state of infection).

Various factors can influence the actual effective amount used for a particular application. For example, the frequency of administration, duration of treatment, use of multiple treatment agents, route of administration, and severity of the viral infection (e.g., picornavirus or herpesvirus infection) may require an increase or decrease in the actual effective amount administered.

The frequency of administration of a picornavirus 3Dpol polypeptide (or fragment thereof) or a nucleic acid encoding a picornavirus 3Dpol polypeptide (or fragment thereof) can be any frequency that reduces severity of a symptom of a viral infection (e.g., a picornavirus infection or a non-picornavirus infection such as herpesvirus infection) without producing significant toxicity to the mammal. For example, the frequency of administration can be from about three times a day to about twice a month, or from about once a week to about once a month, or from about once every other day to about once a week, or from about once a month to twice a year, or from about four times a year to once every five years, or from about once a year to once in a lifetime. The frequency of administration can remain constant or can be variable during the duration of treatment. For example, a nucleic acid encoding a picornavirus 3Dpol polypeptide can be administered daily, twice a day, five days a week, or three days a week. A nucleic acid encoding a picornavirus 3Dpol polypeptide can be administered for five days, 10 days, three weeks, four weeks, eight weeks, 48 weeks, one year, 18 months, two years, three years, or five years. In some cases, a viral vector can be administered as needed. A course of treatment can include rest periods. For example, a nucleic acid encoding a picornavirus 3Dpol polypeptide can be administered for five days followed by a nine-day rest period, and such a regimen can be repeated multiple times. As with the effective amount, various factors can influence the actual frequency of administration used for a particular application. For example, the effective amount, duration of treatment, use of multiple treatment agents, route of administration, and severity of the viral infection may require an increase or decrease in administration frequency.

An effective duration for administering a picornavirus 3Dpol polypeptide (or fragment thereof) or a nucleic acid provided herein can be any duration that reduces the severity of a symptom of a viral infection (e.g., a picornavirus infection or a non-picornavirus infection such as a herpesvirus infection) or achieves a particular level of nucleic acid (e.g., RNA) or picornavirus 3Dpol polypeptide expression without producing significant toxicity to the mammal. Thus, the effective duration can vary from several days to several weeks, months, or years. In general, the effective duration for the treatment of a viral infection can range in duration from several days to several weeks or longer. In some cases, an effective duration can be for several months to a year. Multiple factors can influence the actual effective duration used for a particular treatment. For example, an effective duration can vary with the frequency of administration, effective amount, use of multiple treatment agents, route of administration, and severity of the viral infection.

Any appropriate method can be used to determine whether or not an administered nucleic acid resulted in an increased level of the nucleic acid and/or an increased level of picornavirus 3Dpol RNA or polypeptide. Any appropriate method can be used to determine whether or not administered RNA encoding a picornavirus 3Dpol polypeptide (or fragment thereof) resulted in an increased level of the encoded polypeptide or polypeptide fragment within a mammal. For example, picornavirus 3Dpol polypeptide levels can be detected using any standard antibody based assays such as immunoprecipitation, western hybridization, and sandwich enzyme-linked immunosorbent assays (ELISA). Antibody based assays can utilize combinations of antibodies that bind to one or more sites of the amino-terminal, central, and carboxy-terminal portions of a picornavirus 3Dpol polypeptide. In some cases, the level of a picornavirus 3Dpol transcript can be determined by measuring RNA levels using any appropriate method such as northern blotting, quantitative RT-PCR, microarray analysis, or in situ hybridization.

In some cases, RNA encoding a picornavirus 3Dpol polypeptide (e.g., a composition containing a substantially pure preparation of picornavirus 3Dpol RNA) can be administered instead of or in combination with DNA encoding a picornavirus 3Dpol polypeptide as described herein. In some cases, a substantially pure preparation of picornavirus 3Dpol polypeptide (or fragment thereof) can be administered instead of or in combination with DNA or RNA encoding a picornavirus 3Dpol polypeptide as described herein.

The invention will be further described in the following examples, which do not limit the scope of the invention described in the claims.

EXAMPLES

Example 1

Up-Regulation of Innate Immune Effectors Confers Viral Resistance in a Transgenic Mouse Model Generation of 3Dpol Transgenic Mice Transgenic 3Dpol mice were made as described elsewhere (Pavelko et al., *Brain Pathol.,* 17:184-96 (2007)). Transgenic mice were generated by cloning nucleotides 6586-7968, which encodes for the entire 3D polymerase in the DA strain of TMEV (GenBank accession #M20301) into the eukaryotic expression vector pUB6, which contains an upstream human ubiquitin c promoter (Invitrogen, Carlsbad, Calif.). 3Dpol TMEV DNA was amplified by PCR from pDAFL3 and directionally cloned into pUB6 using a BamHI site on the 5' end of the cloned fragment and an EcoRV site on the 3' end. The construct was cloned while maintaining the His Tag included in the vector, thereby allowing the identification of 3Dpol by this marker. This vector was then cut with Bgl II and Pvu II to yield a fragment of 2935 bp. The resulting fragment encoded all 462 amino acids of the viral RNA polymerase, which was then gel purified and sequenced before injection into embryos. The sequence revealed a base pair substitution at nucleotide 7,620. This substitution did not change the codon, leaving the amino acid sequence identical to the sequenced viral 3D polymerase.

The gel purified DNA was injected into FVB embryos for implantation into pseudo-pregnant females. All embryo injections and implantations were done at a core facility. Tail samples from the offspring were used to obtain genomic DNA for determination of transgene integration. DNA samples were screened using primers for the TMEV 3Dpol gene as well as the ubiquitin c promoter region. Thirty-nine potential founder mice containing the 3Dpol were screened for transgene integration, six mice were positive, and two were chosen for breeding based on the highest copy of transgene integration. These mice were used to establish two lines. Line 1 bred well and was used in this study. Line 2 was used in initial experiments, but this line was later eliminated. All mice used were screened by PCR for the presence of the 3Dpol transgene prior to their use in subsequent assays.

FVB-3D transgenic mice were then crossed to Ifnar1$^{-/-}$ mice, Ifngr1$^{-/-}$ mice, Mda5$^{-/-}$ mice or Rag1$^{-/-}$ mice to obtain 3D-Ifnar1$^{-/-}$, 3D-Ifngr1$^{-/-}$, 3D-Mda5$^{-/-}$, or 3D-Rag1$^{-/-}$ mice.

Virus and Infection

Encephalomyocarditis virus (EMCV; ATTC VR-129B strain) was used for all experiments. Mice were injected intraperitoneally with 40 plaque forming units of EMCV in a volume of 100 μL.

Results

The transgenic 3Dpol mice, that expressed a picornaviral RNA-dependent RNA polymerase (3Dpol) and exhibited a viral resistance phenotype, were further analyzed. Encephalomycarditis virus (EMCV) infection induced up-regulation of 36 genes in the spinal cords of infected wild-type FVB mice as compared with uninfected wild-type mice (Table 2). No genes were down-regulated significantly following EMCV infection. Microarray analyses of spinal cords of uninfected 3Dpol mice were conducted and revealed increased levels of 77 genes (>4-fold) including high up-regulation (up to 110-fold induction) of genes of innate immune effectors (Table 3). Ninety seven percent of the genes induced following EMCV infection in wild-type FVB mice were intrinsically up-regulated in uninfected 3Dpol mice. See, e.g., FIG. 4. In addition, no genes were down-regulated significantly in uninfected 3Dpol mice. RT-PCR analysis demonstrated that this effect was not limited to the spinal cord; brain, cerebellum, lung, kidney, liver and heart tissues of uninfected transgenic 3Dpol mice also displayed statistically significant (up to 298-fold) increases in genes of innate immune effectors. See, e.g., FIG. 5. Proteomics studies indicated that the increased levels of transcripts for these innate immune effectors coincided with higher protein concentrations in tissues of uninfected transgenic mice See, e.g., FIG. 6. In addition, studies of 3D-Ifnar1$^{-/-}$, 3D-Mda5$^{-/-}$, or 3D-Ifngr1$^{-/-}$ mice, supported the conclusion that MDA5-mediated type I IFN signaling is necessary for the antiviral state in 3Dpol mice, whereas IFNg signaling is dispensable. Maintenance of a viral-resistant state in uninfected 3Dpol mice is independent of adaptive immunity since uninfected 3D-Rag1$^{-/-}$ mice are able to highly upregulate antiviral factors. See, e.g., FIG. 7.

TABLE 2

List of genes up-regulated in virally-infected wild-type mice.

| Probeset ID | Gene Title and Symbol | GenBank Accession Number | Fold Change | P-value |
|---|---|---|---|---|
| 1450783_at | interferon-induced protein with tetratricopeptide repeats 1 (Ifit1, Isg56) | NM_008331 | 22.616 | 0.0042 |
| 1418191_at | ubiquitin specific peptidase 18 (Usp18, Ubp43) | NM_011909 | 21.528 | 0.0062 |
| 1449009_at | T-cell specific GTPase 2 (Tgtp2) | NM_001145164 | 20.594 | 0.0086 |
| 1449025_at | interferon-induced protein with tetratricopeptide repeats 3 (Ifit3, Isg49) | NM_010501 | 19.775 | 0.0032 |
| 1419043_a_at | interferon inducible GTPase 1 (Iigp1) | NM_001146275 | 13.848 | 0.0127 |
| 1457666_s_at | interferon activated gene 202B (Ifi202b) | NM_008327 | 12.318 | 0.0029 |
| 1423555_a_at | interferon-induced protein 44 (Ifi44) | NM_133871 | 11.793 | 0.0065 |
| 1453196_a_at | 2'-5' oligoadenylate synthetase-like 2 (Oasl2) | NM_011854 | 11.047 | 0.0061 |
| 1426278_at | interferon, alpha-inducible protein 27 like 2A (Ifi27l2a) | NM_029803 | 10.258 | 0.0011 |
| 1419042_at | interferon inducible GTPase 1 (Iigp1) | NM_001146275 | 10.063 | 0.0121 |
| 1418580_at | receptor transporter protein 4 (Rtp4) | NM_023386 | 9.370 | 0.0040 |
| 1431591_s_at | ISG15 ubiquitin-like modifier (Isg15) | NM_015783 | 9.251 | 0.0077 |
| 1451860_a_at | tripartite motif-containing 30 (Trim30a) | NM_009099 | 8.808 | 0.0082 |
| 1434380_at | guanylate binding protein 7 (Gbp7) | NM_001083312 | 8.078 | 0.0058 |
| 1417793_at | immunity-related GTPase family M member 2 (Irgm2) | NM_019440 | 7.633 | 0.0194 |
| 1421009_at | radical S-adenosyl methionine domain containing 2 (Rsad2, Viperin) | NM_021384 | 6.201 | 0.0059 |
| 1429184_at | GTPase, very large interferon inducible 1 (Gvin1) | NM_001039160 | 6.158 | 0.0084 |
| 1439831_at | — | — | 5.982 | 0.0168 |
| 1417141_at | interferon gamma induced GTPase (Igtp, Irgm3) | NM_018738 | 5.953 | 0.0156 |
| 1418392_a_at | guanylate binding protein 3 (Gbp3) | NM_018734 | 5.640 | 0.0021 |
| 1417292_at | interferon gamma inducible protein 47 (Ifi47, Irg47) | NM_008330 | 5.538 | 0.0081 |
| 1421551_s_at | interferon activated gene 202B (Ifi202b) | NM_008327 | 5.519 | 0.0138 |
| 1451564_at | poly (ADP-ribose) polymerase family, member 14 (Parp14) | NM_001039530 | 5.369 | 0.0065 |
| 1436058_at | radical S-adenosyl methionine domain containing 2 (Rsad2, Viperin) | NM_021384 | 5.329 | 0.0080 |
| 1426276_at | melanoma differentiation-associated gene 5 (Mda5, Ifih1) | NM_001164477 | 5.311 | 0.0122 |
| 1451777_at | DEAD (Asp-Glu-Ala-Asp) box polypeptide 60 (Ddx60) | NM_001081215 | 5.156 | 0.0079 |
| 1447927_at | guanylate binding protein 10 (Gbp10) | NM_001039646 | 5.125 | 0.0188 |
| 1425156_at | guanylate binding protein 7 (Gbp7) | NM_001083312 | 5.038 | 0.0078 |
| 1424775_at | 2'-5' oligoadenylate synthetase 1A (Oas1a) | NM_145211 | 5.021 | 0.0036 |
| 1418240_at | guanylate binding protein 2 (Gbp2) | NM_010260 | 4.968 | 0.0308 |
| 1438676_at | guanylate binding protein 6 (Gbp6, Mpa2l) | NM_194336 | 4.654 | 0.0190 |
| 1419282_at | chemokine (C-C motif) ligand 12 (Ccl12) | NM_011331 | 4.653 | 0.0428 |
| 1435906_x_at | guanylate binding protein 2 (Gbp2) | NM_010260 | 4.647 | 0.0246 |
| 1417244_a_at | interferon regulatory factor 7 (Irf7) | NM_016850 | 4.645 | 0.0053 |
| 1425974_a_at | tripartite motif-containing 25 (Trim25) | NM_009546 | 4.608 | 0.0085 |
| 1437176_at | NLR family, CARD domain containing 5 (Nlrc5) | NM_001033207 | 4.492 | 0.0246 |
| 1435331_at | pyrin and HIN domain family, member 1 (Pyhin1) | NM_175026 | 4.484 | 0.0154 |
| 1451335_at | placenta-specific 8 (Plac8, Onzin) | NM_139198 | 4.349 | 0.0070 |
| 1460603_at | sterile alpha motif domain containing 9-like (Samd9l) | NM_010156 | 4.286 | 0.0072 |
| 1418776_at | guanylate-binding protein 8 (Gbp8) | NM_029509 | 4.239 | 0.0395 |
| 1416897_at | poly (ADP-ribose) polymerase family, member 9 (Parp9) | NM_030253 | 4.211 | 0.0069 |
| 1450033_a_at | signal transducer and activator of transcription 1 (Stat1) | NM_009283 | 4.181 | 0.0027 |
| 1456890_at | Retinoic acid-inducible gene l protein (Rig-1, Ddx58) | NM_172689 | 4.037 | 0.0105 |
| 1419879_s_at | tripartite motif-containing 25 (Trim25) | NM_009546 | 4.003 | 0.0116 |

TABLE 3

List of genes up-regulated in uninfected 3Dpol mice.

| Probeset ID | Gene Title and Symbol | GenBank Accession Number | Fold Change | P-value |
|---|---|---|---|---|
| 1418191_at | ubiquitin specific peptidase 18 (Usp18, Ubp43) | NM_011909 | 109.987 | 3.01E−08 |
| 1426278_at | interferon, alpha-inducible protein 27 like 2A (Ifi27l2a) | NM_029803 | 97.3729 | 7.99E−07 |
| 1453196_a_at | 2'-5' oligoadenylate synthetase-like 2 (Oasl2) | NM_011854 | 90.859 | 5.38E−07 |
| 1423555_a_at | interferon-induced protein 44 (Ifi44) | NM_133871 | 64.1228 | 2.84E−07 |
| 1450783_at | interferon-induced protein with tetratricopeptide repeats 1 (Ifit1, Isg56) | NM_008331 | 58.999 | 1.37E−07 |
| 1419043_a_at | interferon inducible GTPase 1 (Iigp1) | NM_001146275 | 40.7201 | 3.47E−06 |
| 1431591_s_at | ISG15 ubiquitin-like modifier (Isg15) | NM_015783 | 37.4158 | 3.39E−07 |
| 1419042_at | interferon inducible GTPase 1 (Iigp1) | NM_001146275 | 28.9041 | 9.17E−07 |
| 1449025_at | interferon-induced protein with tetratricopeptide repeats 3 (Ifit3, Isg49) | NM_010501 | 28.3864 | 3.97E−06 |
| 1418580_at | receptor transporter protein 4 (Rtp4) | NM_023386 | 25.7496 | 1.41E−07 |
| 1439831_at | — | — | 24.7817 | 6.65E−06 |
| 1418392_a_at | guanylate binding protein 3 (Gbp3) | NM_018734 | 23.6396 | 8.27E−06 |
| 1457666_s_at | interferon activated gene 202B (Ifi202b) | NM_008327 | 20.6935 | 4.10E−06 |
| 1451777_at | DEAD (Asp-Glu-Ala-Asp) box polypeptide 60 (Ddx60) | NM_001081215 | 19.7676 | 6.33E−07 |
| 1424518_at | apolipoprotein L 9a (Apol9a) | NM_001162883 | 19.5138 | 1.76E−08 |
| 1449009_at | T-cell specific GTPase 2 (Tgtp2) | NM_001145164 | 18.839 | 3.37E−05 |
| 1424921_at | bone marrow stromal cell antigen 2 (Bst2, Tetherin) | NM_198095 | 17.7718 | 2.71E−05 |
| 1424775_at | 2'-5' oligoadenylate synthetase 1A (Oas1a) | NM_145211 | 16.9493 | 1.44E−06 |
| 1451860_a_at | tripartite motif-containing 30A (Trim30a) | NM_009099 | 16.8475 | 1.17E−06 |
| 1438676_at | guanylate binding protein 6 (Gbp6, Mpa2l) | NM_194336 | 16.5069 | 1.13E−06 |
| 1447927_at | guanylate binding protein 10 (Gbp10) | NM_001039646 | 15.9636 | 7.17E−07 |
| 1421009_at | radical S-adenosyl methionine domain containing 2 (Rsad2, Viperin) | NM_021384 | 14.3738 | 1.58E−06 |
| 1418930_at | chemokine (C-X-C motif) ligand 10 (Cxcl10) | NM_021274 | 14.3572 | 1.24E−06 |
| 1460603_at | sterile alpha motif domain containing 9-like (Samd9l) | NM_010156 | 11.5764 | 2.03E−06 |
| 1439114_at | DEAD (Asp-Glu-Ala-Asp) box polypeptide 60 (Ddx60) | NM_001081215 | 11.0017 | 8.28E−06 |
| 1434380_at | guanylate binding protein 7 (Gbp7) | NM_001083312 | 10.9977 | 2.52E−06 |
| 1421551_s_at | interferon activated gene 202B (Ifi202b) | NM_008327 | 10.563 | 7.67E−06 |
| 1431008_at | histocompatibility 2, Q region locus 6/// histocompatibility 2, Q region locus (H2-Q6) | NM_207648 | 10.4958 | 1.09E-06 |
| 1417961_a_at | tripartite motif-containing 30A (Trim30a) | NM_009099 | 10.3521 | 2.04E−08 |
| 1438037_at | hect domain and RLD 6 (Herc6, Herc5) | NM_025992 | 10.3228 | 1.64E−06 |
| 1417793_at | immunity-related GTPase family M member 2 (Irgm2) | NM_019440 | 10.201 | 7.12E−06 |
| 1443698_at | XIAP associated factor 1 (Xaf1) | NM_001037713 | 9.93139 | 5.19E−05 |
| 1436058_at | radical S-adenosyl methionine domain containing 2 (Rsad2, Viperin) | NM_021384 | 9.87972 | 1.70E−05 |
| 1450034_at | signal transducer and activator of transcription 1 (Stat1) | NM_009283 | 9.60695 | 3.11E−07 |
| 1451335_at | placenta-specific 8 (Plac8, Onzin) | NM_139198 | 9.39134 | 1.45E−06 |
| 1426276_at | melanoma differentiation-associated gene 5 (Mda5, Ifih1) | NM_001164477 | 9.2899 | 9.41E−06 |
| 1451655_at | schlafen 8 (Slfn8) | NM_001167743 | 9.24169 | 2.22E−05 |
| 1420915_at | signal transducer and activator of transcription 1 (Stat1) | NM_009283 | 9.12678 | 2.14E−06 |
| 1449556_at | histocompatibility 2, T region locus 23 (H2-T23) | NM_010398 | 9.1173 | 2.34E−06 |
| 1448380_at | lectin, galactoside-binding, soluble, 3 binding protein (Lgals3bp, CyCap) | NM_011150 | 8.88822 | 3.28E−06 |
| 1417244_a_at | interferon regulatory factor 7 (Irf7) | NM_016850 | 8.78038 | 2.09E−06 |
| 1456890_at | Retinoic acid-inducible gene l protein (Rig-1, Ddx58) | NM_172689 | 8.61271 | 9.63E−07 |

TABLE 3-continued

List of genes up-regulated in uninfected 3Dpol mice.

| Probeset ID | Gene Title and Symbol | GenBank Accession Number | Fold Change | P-value |
|---|---|---|---|---|
| 1421322_a_at | interferon regulatory factor 9 (Irf9) | NM_001159417 | 8.39351 | 5.90E−07 |
| 1450033_a_at | signal transducer and activator of transcription 1 (Stat1) | NM_009283 | 8.27923 | 2.95E−06 |
| 1425156_at | guanylate binding protein 7 (Gbp7) | NM_001083312 | 8.23142 | 5.21E−06 |
| 1418825_at | immunity-related GTPase family M member 1 (Irgm1) | NM_008326 | 8.04395 | 4.58E−06 |
| 1452178_at | plectin (Plec) | NM_001163540 | 7.54397 | 2.64E−06 |
| 1417292_at | interferon gamma inducible protein 47 (Ifi47) | NM_008330 | 7.30315 | 6.24E−05 |
| 1421217_a_at | lectin, galactose binding, soluble 9 (Lgals9, Gal-9) | NM_001159301 | 7.30251 | 6.23E−05 |
| 1418293_at | interferon-induced protein with tetratricopeptide repeats 2 (Ifit2, Isg54) | NM_008332 | 7.275 | 8.50E−06 |
| 1419282_at | chemokine (C-C motif) ligand 12 (Ccl12) | NM_011331 | 7.20807 | 5.25E−05 |
| 1451644_a_at | histocompatibility 2, Q region locus 4 (H2-Q4) | NM_001143689 | 7.18918 | 1.87E−05 |
| 1417141_at | interferon gamma induced GTPase (Igtp, Irgm3) | NM_018738 | 7.04585 | 2.34E−05 |
| 1451564_at | poly (ADP-ribose) polymerase family, member 14 (Parp14) | NM_001039530 | 6.79057 | 2.30E−05 |
| 1435792_at | component of Sp100-rs (Csprs, Hsr) | NM_033616 | 6.65655 | 4.23E−06 |
| 1440481_at | signal transducer and activator of transcription 1 (Stat1) | NM_009283 | 6.53919 | 1.31E−05 |
| 1445897_s_at | interferon-induced protein 35 (Ifi35) | NM_027320 | 6.39344 | 1.77E−06 |
| 1422962_a_at | proteasome (prosome, macropain) subunit, beta type 8 (Psmb8) | NM_010724 | 6.34633 | 5.32E−06 |
| 1435331_at | pyrin and HIN domain family, member 1 (Pyhin1) | NM_175026 | 6.23643 | 3.21E−06 |
| 1423754_at | interferon induced transmembrane protein 3 (Ifitm3) | NM_025378 | 6.03863 | 3.22E−05 |
| 1436183_at | zinc finger CCCH type, antiviral 1 (Zap, Zc3hav1) | NM_028421 | 5.8746 | 7.65E−06 |
| 1435665_at | tripartite motif-containing 30D (Trim30d, Trim30-3) | NM_001167828 | 5.86904 | 1.82E−05 |
| 1426774_at | poly (ADP-ribose) polymerase family, member 12 (Parp12) | NM_172893 | 5.79399 | 5.51E−07 |
| 1425974_a_at | tripartite motif-containing 25 (Trim25) | NM_009546 | 5.6636 | 1.29E−05 |
| 1417185_at | lymphocyte antigen 6 complex, locus A (Ly6a) | NM_010738 | 5.6258 | 8.33E−06 |
| 1419879_s_at | tripartite motif-containing 25 (Trim25) | NM_009546 | 5.57849 | 1.16E−05 |
| 1429184_at | GTPase, very large interferon inducible 1 (Gvin1) | NM_001039160 | 5.50519 | 6.17E−05 |
| 1436562_at | Retinoic acid-inducible gene l protein (Rig-1, Ddx58) | NM_172689 | 5.50506 | 2.72E−05 |
| 1425336_x_at | histocompatibility 2, K1, K region (H2-K1) | NM_001001892 | 5.39799 | 1.20E−05 |
| 1440866_at | eukaryotic translation initiation factor 2-alpha kinase 2///protein kinase R (Eif2ak2, Pkr) | NM_011163 | 5.37645 | 1.60E−04 |
| 1418126_at | chemokine (C-C motif) ligand 5 (Ccl5) | NM_013653 | 5.36097 | 3.44E−06 |
| 1437176_at | NLR family, CARD domain containing 5 (Nlrc5) | NM_001033207 | 5.34208 | 3.38E−05 |
| 1451426_at | DEXH (Asp-Glu-X-His) box polypeptide 58 (Dhx58, Lgp2) | NM_030150 | 5.26226 | 1.23E−05 |
| 1451905_a_at | myxovirus (influenza virus) resistance 1 (Mx1) | NM_010846 | 5.18634 | 7.99E−05 |
| 1416897_at | poly (ADP-ribose) polymerase family, member 9 (Parp9) | NM_030253 | 5.14995 | 2.65E−05 |
| 1432026_a_at | hect domain and RLD 6 (Herc6, Herc5) | NM_025992 | 5.11761 | 6.55E−05 |
| 1424948_x_at | histocompatibility 2, K1, K region (H2-K1) | NM_001001892 | 5.07903 | 1.46E−06 |
| 1449289_a_at | beta-2 microglobulin (B2m) | NM_009735 | 5.06409 | 7.03E−05 |
| 1426324_at | histocompatibility 2, D region locus 1 (H2-D1) | NM_010380 | 5.03837 | 6.16E−06 |
| 1443858_at | tripartite motif-containing 12c (Trim12c, Trim12-2) | NM_001146007 | 5.03457 | 8.39E−07 |

TABLE 3-continued

List of genes up-regulated in uninfected 3Dpol mice.

| Probeset ID | Gene Title and Symbol | GenBank Accession Number | Fold Change | P-value |
|---|---|---|---|---|
| 1456494_a_at | tripartite motif-containing 30D (Trim30d, Trim30-3) | NM_001167828 | 5.01172 | 1.68E−06 |
| 1435906_x_at | guanylate binding protein 2 (Gbp2) | NM_010260 | 4.9742 | 1.82E−04 |
| 1421008_at | radical S-adenosyl methionine domain containing 2 (Rsad2, Viperin) | NM_021384 | 4.97238 | 4.12E−05 |
| 1426971_at | ubiquitin-like modifier activating enzyme 7 (Uba7, Ube1l) | NM_023738 | 4.93456 | 1.46E−04 |
| 1450696_at | proteasome (prosome, macropain) subunit, beta type 9 (Psmb9) | NM_013585 | 4.90847 | 5.73E−05 |
| 1454757_s_at | interferon, alpha-inducible protein 27 like 1 (Ifi27l1) | NM_026790 | 4.78979 | 3.56E−06 |
| 1436172_at | predicted gene 20559 (Gm20559) | XR_104969 | 4.78227 | 8.15E−05 |
| 1452428_a_at | beta-2 microglobulin (B2m) | NM_009735 | 4.73207 | 1.22E−05 |
| 1418240_at | guanylate binding protein 2 (Gbp2) | NM_010260 | 4.66603 | 1.29E−04 |
| 1451683_x_at | histocompatibility 2, D region locus 1 (H2-D1) | NM_010380 | 4.64058 | 4.17E−04 |
| 1435208_at | deltex 3-like (Dtx3l) | NM_001013371 | 4.54289 | 2.05E−07 |
| 1450291_s_at | membrane-spanning 4-domains, subfamily A, member 4C (Ms4a4c) | NM_029499 | 4.51925 | 9.87E−05 |
| 1417851_at | chemokine (C-X-C motif) ligand 13 (Cxcl13) | NM_018866 | 4.51033 | 5.08E−05 |
| 1455500_at | ring finger protein 213 (Rnf213) | XM_001476651 | 4.45569 | 4.93E−05 |
| 1422005_at | eukaryotic translation initiation factor 2-alpha kinase 2///protein kinase R (Eif2ak2, Pkr) | NM_011163 | 4.45197 | 4.30E−06 |
| 1439825_at | deltex 3-like (Dtx3l) | NM_001013371 | 4.43139 | 1.04E−06 |
| 1418536_at | histocompatibility 2, Q region locus 7 (H2-Q7) | NM_001198560 | 4.38716 | 2.93E−06 |
| 1424339_at | 2'-5' oligoadenylate synthetase-like 1 (Oasl1) | NM_145209 | 4.37953 | 1.33E−04 |
| 1449143_at | receptor transporter protein 4 (Rtp4) | NM_023386 | 4.36937 | 1.77E−06 |
| 1424617_at | interferon-induced protein 35 (Ifi35) | NM_027320 | 4.3009 | 1.96E−05 |
| 1419676_at | myxovirus (influenza virus) resistance 2 (Mx2) | NM_013606 | 4.2255 | 3.09E−06 |
| 1452956_a_at | interferon, alpha-inducible protein 27 like 1 (Ifi27l1) | NM_026790 | 4.18437 | 2.61E−06 |
| 1438027_at | — | — | 4.07252 | 2.21E−04 |

These results demonstrate that prior to viral infection, 3Dpol transgenic mice were primed and equipped with many of the effectors of an innate immune response. The cells of transgenic 3Dpol mice were advantageously apportioned with effectors that promptly recognized and readily eliminated viral presence. This aggrandized innate immune response can help explain the reduction in viral titers, preservation of tissue integrity, and enhanced survival that is characteristic of the 3Dpol mouse model. Collectively, these results indicate that intrinsic upregulation of critical innate immune effectors confers broad-spectrum viral resistance in 3Dpol mice.

Example 2

Using Lentiviral Vectors to Treat Viral Infections

A nucleic acid encoding a picornavirus 3Dpol polypeptide is administered to a mammal using a viral vector. Such a lentiviral vector is administered to a mammal to induce expression of a set of nucleic acids that encode polypeptides involved in innate immunity. Vectors for administering nucleic acids (e.g., a nucleic acid encoding a picornavirus 3Dpol polypeptide) to a mammal are prepared using standard materials (e.g., packaging cell lines, helper viruses, and vector constructs). See, for example, *Gene Therapy Protocols* (*Methods in Molecular Medicine*), edited by Jeffrey R. Morgan, Humana Press, Totowa, N.J. (2002) and *Viral Vectors for Gene Therapy: Methods and Protocols*, edited by Curtis A. Machida, Humana Press, Totowa, N.J. (2003). Virus-based nucleic acid delivery vectors are derived from animal viruses, such as adenoviruses, adeno-associated viruses, retroviruses, lentiviruses, vaccinia viruses, herpes viruses, and papilloma viruses. Vectors for nucleic acid delivery are genetically modified such that the pathogenicity of the virus is altered or removed. The genome of a virus is modified to increase infectivity and/or to accommodate packaging of a nucleic acid, such as a nucleic acid encoding a picornavirus 3Dpol polypeptide. A viral vector is replication-competent or replication-defective, and contains fewer viral genes than a corresponding wild-type virus or no viral genes at all.

In addition to nucleic acid encoding a picornavirus 3Dpol polypeptide, a lentiviral vector contains regulatory elements operably linked to a nucleic acid encoding a picornavirus 3Dpol polypeptide. Such regulatory elements include promoter sequences, enhancer sequences, response elements, signal peptides, internal ribosome entry sequences, polyadenylation signals, terminators, or inducible elements that modulate expression (e.g., transcription or translation) of a nucleic acid. The choice of element(s) included in a viral vector depends on several factors including, without limitation, inducibility, targeting, and the level of expression desired. For example, a promoter is included in a viral vector to facilitate transcription of a nucleic acid encoding a picornavirus 3Dpol polypeptide. A promoter is constitutive or inducible (e.g., in the presence of tetracycline), and can affect the expression of a nucleic acid encoding a picornavirus 3Dpol polypeptide in a general or tissue-specific manner.

General promoters include, without limitation, cytomegalovirus (CMV) promoters and ubiquitin promoters. In this way, a lentiviral construct based therapeutic is constructed using general promoters and the 3Dpol transgene sequence designed to express the 3D trangene in all tissues of the organism. Animals or humans are treated with a 3D lentiviral vector before possible exposure to a virus or following contact or known infection with a virus. 3D lentiviral vector can be given as a single iv dose, or as multiple doses. 3D lentivirus efficacy is judged by reducing clinical symptoms of viral infection and increasing survival of a treated population.

Tissue-specific promoters include, without limitation, neuron specific enolase promoters for neurons, glial fibrillary acidic protein (GFAP) promoters for astrocytes, and myelin basic protein (MBP) promoters for oligodendrocytes. For example, a viral vector can contain an oligodendrocyte-specific MBP promoter and a nucleic acid encoding a picornavirus 3Dpol polypeptide. In this case, the MBP promoter is operably linked to a nucleic acid encoding a picornavirus 3Dpol polypeptide such that it drives transcription in oligodendrocytes of the central nervous system. Targeting lentiviral vectors expressing 3Dpol are constructed using tissue-specific promoters. In this way, following lentiviral vector treatment, the 3D transgene is expressed in specific tissues. Examples include use of a liver-specific promoter, such as the Lap/Cebpb promoter, for liver-specific 3D expression to protect or clear hepatotropic viruses such as Hepatitis C. Furthermore, a heart-specific promoter, such as the Myh6 promoter, can be used for heart specific-3D expression to protect or clear cardiomyotropic viruses such as Coxsackie B.

Patients to treat with 3Dpol lentiviral vectors are identified by having a systemic or tissue-specific viral infection or at risk of being virally infected. Any appropriate method is used to identify a patient having a viral infection. For example, PCR-based assays such as those that quantify viral transcripts, e.g., in the tissue, saliva, or stool as is appropriate for the specific virus by real-time quantitative PCR, or a serological assay that quantifies viral specific IgM or IgG are used to identify a patient having a viral infection.

The appropriate tissue-specific or non-tissue specific 3Dpol lentiviral construct is administered. A human having a viral infection (e.g., a picornavirus infection or a non-picornavirus infection such as a herpesvirus infection) is treated by administering lentiviral vector encoding DNA, RNA, or a combination of picornavirus 3Dpol polypeptide. Lentiviral vectors encoding the complete DNA or RNA or a combination of the picornavirus 3Dpol polypeptide and/or a picornavirus 3Dpol polypeptide is used. Alternatively, lentiviral vectors encoding a fragment of DNA or RNA or a combination of the picornavirus 3Dpol polypeptide and/or a picornavirus 3Dpol polypeptide is used. In some cases, a 3Dpol lentivirus vector is administered to patients with the goal of reducing or preventing future viral infections, such as before travel to an area with prevalent viruses or in the theater of war where biologic weapons may be used. Since innate immune effectors activated by 3Dpol lentiviral vectors are not pathogen-specific, 3Dpol lentiviral treatment can attenuate infection and diseases caused by viruses outside the picornavirus family including, without limitation, herpesvirus, retrovirus, orthomyxovirus, filovirus, flavivirus, and hepadnavirus infections.

In addition, any appropriate mammal is treated with the appropriate lentiviral vectors including, without limitation, humans, cows, pigs, sheep, horses, goats, llamas, elk, deer, dogs, cats, and bison. Any appropriate method is used to identify a mammal having a viral infection or at risk of being virally infected. For example, PCR-based assays such as those that quantify viral transcripts, e.g., in the tissue, saliva, or stool as is appropriate for the specific virus by real-time quantitative PCR, or a serological assay that quantifies viral specific IgM or IgG is used to identify a mammal having a viral infection. Once identified, a mammal having a viral infection or at risk of a viral infection is treated by administering the appropriate tissue specific or non-tissue specific 3Dpol lentiviral construct.

Lentiviral vectors encoding a picornavirus 3Dpol polypeptide (e.g., a recombinant viral vector) are administered to a patient or mammal using any appropriate method, including orally, nasally, or by injection. A composition including a viral vector is in liquid form (e.g., solutions, solvents, suspensions, and emulsions) and includes sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. 3Dpol lentiviral vectors are prepared in solid (e.g., lyophilized) form for administration following addition of any appropriate diluent, such as a saline diluent (e.g., 0.4% or 0.9% sodium chloride, pH 7.4).

Suitable formulations for oral administration include tablets or capsules prepared by conventional means with pharmaceutically acceptable excipients such as binding agents (e.g., pregelatinized maize starch, polyvinylpyrrolidone or hydroxypropyl methylcellulose), fillers (e.g., lactose, microcrystalline cellulose or calcium hydrogen phosphate), lubricants (e.g., magnesium stearate, talc or silica), disintegrants (e.g., potato starch or sodium starch glycolate), or wetting agents (e.g., sodium lauryl sulfate). Tablets are coated by methods known in the art. Preparations for oral administration are formulated for controlled release of the lentiviral vector encoding a picornavirus 3Dpol polypeptide.

Intranasal preparations are presented in a liquid form (e.g., nasal drops or aerosols) or as a dry product (e.g., a powder). Both liquid and dry nasal preparations are administered using a suitable inhalation device. Nebulized aqueous suspensions or solutions are prepared with or without a suitable pH and/or tonicity adjustment.

A lentiviral vector encoding a picornavirus 3Dpol polypeptide is administered to a mammal or human in any amount, at any frequency, and for any duration effective to achieve a desired outcome (e.g., to reduce a symptom of a picornavirus or a non-picornavirus such as a herpesvirus infection). In some cases, a lentiviral vector encoding a picornavirus 3Dpol polypeptide is administered to a mammal to reduce a symptom of a picornavirus or herpesvirus infection by 5, 10, 25, 50, 75, 100, or more percent. Any appropriate method is used to determine whether or not a symptom of a viral infection is reduced. For example, a motor function test, or walking ability, is used for poliomyelitis or observation of appetite and weight increase as well as decreased malaise and sores is used for foot and mouth disease. In some cases, a lentivral vector encoding a picornavirus 3Dpol polypeptide is administered to a mammal or human to reduce the severity or to delay the onset of a severe viral infection (e.g., a severe picornavirus infection).

An effective amount of a lentiviral vector encoding a picornavirus 3Dpol polypeptide is any amount that reduces a symptom of a viral infection (e.g., a picornavirus or herpesvirus infection) without producing significant toxicity. In some cases, the effective amount of lentivral vector encoding a picornavirus 3Dpol polypeptide can be between 0.1 µg/kg and 750 µg/kg (e.g., between 1 µg/kg and 500 µg/kg, between 10 µg/kg and 500 µg/kg, between 100 µg/kg and 500 µg/kg, between 1 µg/kg and 250 µg/kg, between 1 µg/kg and 100 µg/kg, between 10 µg/kg and 400 µg/kg, between 10 µg/kg and 250 µg/kg). In some cases, an effective amount of lentiviral vector encoding a picornavirus 3Dpol polypeptide can be from about $10^3$ to $10^{12}$ (e.g., about $10^8$) recombinant viral particles or plaque forming units (pfu) containing the nucleic acid. If a particular mammal fails to respond to a particular amount, then the amount is increased by, for example, ten fold. After receiving this higher concentration, the mammal is monitored for both responsiveness to the treatment and toxicity symptoms, and adjustments made accordingly. The effective amount remains constant or is adjusted as a sliding scale or variable dose depending on the mammal's response to treatment (e.g., the mammal's level of picornavirus 3Dpol RNA or polypeptides or the mammal's state of infection).

Various factors influence the actual effective amount of lentiviral vector used for a particular application. For example, the frequency of administration, duration of treatment, use of multiple treatment agents, route of administration, and severity of the viral infection (e.g., picornavirus or herpesvirus infection) may require an increase or decrease in the actual effective amount administered.

The frequency of administration of lentiviral vector encoding a picornavirus 3Dpol polypeptide is any frequency that reduces severity of a symptom of a viral infection (e.g., a picornavirus infection or a non-picornavirus infection such as herpesvirus infection) without producing significant toxicity to the mammal. For example, the frequency of administration is from about three times a day to about twice a month, or from about once a week to about once a month, or from about once every other day to about once a week, or from about once a month to twice a year, or from about four times a year to once every five years, or from about once a year to once in a lifetime. The frequency of administration can remain constant or can be variable during the duration of treatment. For example, lentiviral vector encoding a picornavirus 3Dpol polypeptide is administered daily, twice a day, five days a week, or three days a week. A lentiviral vector encoding a picornavirus 3Dpol polypeptide is administered for five days, 10 days, three weeks, four weeks, eight weeks, 48 weeks, one year, 18 months, two years, three years, or five years. A course of treatment can include rest periods. For example, a lentiviral vector encoding a picornavirus 3Dpol polypeptide is administered for five days followed by a nine-day rest period, and such a regimen is repeated multiple times. As with the effective amount, various factors can influence the actual frequency of administration used for a particular application. For example, the effective amount, duration of treatment, use of multiple treatment agents, route of administration, and severity of the viral infection may require an increase or decrease in administration frequency.

An effective duration for administering a lentiviral vector provided herein is any duration that reduces the severity of a symptom of a viral infection (e.g., a picornavirus infection or a non-picornavirus infection such as a herpesvirus infection) or achieves a particular level of nucleic acid (e.g., RNA) or picornavirus 3Dpol polypeptide expression without producing significant toxicity to the mammal. Thus, the effective duration can vary from several days to several weeks, months, or years. In general, the effective duration for the treatment of a viral infection can range in duration from several days to several weeks or longer. In some cases, an effective duration can be for several months to a year. Multiple factors can influence the actual effective duration used for a particular treatment. For example, an effective duration can vary with the frequency of administration, effective amount, use of multiple treatment agents, route of administration, and severity of the viral infection.

Any appropriate method can be used to determine whether or not an administered lentiviral vector resulted in an increased level of the nucleic acid and/or an increased level of picornavirus 3Dpol RNA or polypeptide. Any appropriate method is used to determine whether or not administered lentiviral vector encoding a picornavirus 3Dpol polypeptide (or fragment thereof) results in an increased level of the encoded polypeptide or polypeptide fragment within a mammal. For example, picornavirus 3Dpol polypeptide levels are detected using any standard antibody based assays such as immunoprecipitation, western hybridization, and sandwich enzyme-linked immunosorbent assays (ELISA). Antibody based assays utilize combinations of antibodies that bind to one or more sites of the amino-terminal, central, and carboxy-terminal portions of a picornavirus 3Dpol polypeptide. In some cases, the level of a picornavirus 3Dpol transcript is determined by measuring RNA levels using any appropriate method such as northern blotting, quantitative RT-PCR, microarray analysis, or in situ hybridization.

Example 3

Using RNA to Treat Viral Infections

RNA encoding a picornavirus 3Dpol polypeptide is administered to a mammal. The RNA encodes a picornavirus 3Dpol polypeptide having the amino acid sequence set forth in SEQ ID NO:2. Additional examples of nucleic acids that encode a picornavirus 3Dpol polypeptide include, without limitation, those set forth in GenBank® having accession numbers NC_001366 (nucleotides 6594-7976; GI No: 9626123), NC_009448 (nucleotides 6546-7928; GI No: 182406744), NC_001479 (nucleotides 6330-7707; GI No.: 9626692), NC_003982 (nucleotides 6233-7624; GI No: 21328570), NC_004004 (nucleotides 6615-8024; GI No: 21426907), and NC_002058 (nucleotides 5987-7369; GI No: 12408699).

RNA encoding a picornavirus 3Dpol polypeptide is produced by standard techniques, including, without limitation, common molecular cloning, polymerase chain reaction (PCR), chemical nucleic acid synthesis techniques, and combinations of such techniques. For example, PCR or RT-PCR is used with oligonucleotide primers designed to amplify viral nucleic acid encoding a picornavirus 3Dpol polypeptide. Once isolated, the RNA is used for treatment.

Patients to treat with 3Dpol RNA are identified by having a systemic or tissue specific viral infection or at risk of being virally infected. Any appropriate method is used to identify a patient having a viral infection. For example, PCR-based assays such as those that quantify viral transcripts, e.g., in the tissue, saliva, or stool as is appropriate for the specific virus by real-time quantitative PCR, or a serological assay that quantifies viral specific IgM or IgG is used to identify a patient having a viral infection.

In some cases, a 3Dpol RNA is administered to patients with the goal of reducing or preventing future viral infections, such as before travel to an area with prevalent viruses or in the theater of war where biologic weapons may be used. Since innate immune effectors activated by 3Dpol RNA are not pathogen-specific, 3Dpol RNA treatment can attenuate infection by and diseases caused by viruses outside the picornavirus family including, without limitation, herpesvirus, retrovirus, orthomyxovirus, filovirus, flavivirus, and hepadnavirus infections.

In addition, any appropriate mammal is treated with 3Dpol RNA including, without limitation, humans, cows, pigs, sheep, horses, goats, llamas, elk, deer, dogs, cats, and bison. Any appropriate method is used to identify a mammal having a viral infection (e.g., a picornavirus or herpesvirus infection) or at risk of being virally infected. For example, PCR-based assays such as those that quantify viral transcripts, e.g., in the tissue, saliva, or stool as is appropriate for the specific virus by real-time quantitative PCR, or a serological assay that quantifies viral specific IgM or IgG are used to identify a mammal having a viral infection. Once identified, a mammal having a viral infection or at risk of a viral infection is treated by administering RNA encoding a picornavirus 3Dpol polypeptide. In some cases, such administrations are performed under conditions that increase the level of a picornavirus 3Dpol polypeptide in the mammal.

RNA encoding a picornavirus 3Dpol polypeptide is administered to a mammal using non-viral vectors. See, for example, *Gene Therapy Protocols* (*Methods in Molecular Medicine*), edited by Jeffrey R. Morgan, Humana Press, Totowa, N.J. (2002). For example, RNA encoding a picornavirus 3Dpol polypeptide is administered to a mammal by direct injection of RNA molecules (e.g., plasmids) including RNA encoding a picornavirus 3Dpol polypeptide, or by administering RNA complexed with lipids, polymers, or nanospheres. RNA encoding a picornavirus 3Dpol polypeptide is administered to a mammal using any appropriate method. For example, RNA encoding a picornavirus 3Dpol polypeptide is administered orally, nasally, or by injection.

A composition including RNA encoding a picornavirus 3Dpol polypeptide is in liquid form (e.g., solutions, solvents, suspensions, and emulsions) and can include sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. RNA is prepared in solid (e.g., lyophilized) form for administration following addition of any appropriate diluent, such as a saline diluent (e.g., 0.4% or 0.9% sodium chloride, pH 7.4).

Suitable formulations for oral administration include tablets or capsules prepared by conventional means with pharmaceutically acceptable excipients such as binding agents (e.g., pregelatinized maize starch, polyvinylpyrrolidone or hydroxypropyl methylcellulose), fillers (e.g., lactose, microcrystalline cellulose or calcium hydrogen phosphate), lubricants (e.g., magnesium stearate, talc or silica), disintegrants (e.g., potato starch or sodium starch glycolate), or wetting agents (e.g., sodium lauryl sulfate). Tablets are coated by methods known in the art. Preparations for oral administration are formulated to give controlled release of the RNA encoding a picornavirus 3Dpol polypeptide.

Intranasal preparations are presented in a liquid form (e.g., nasal drops or aerosols) or as a dry product (e.g., a powder). Both liquid and dry nasal preparations are administered using a suitable inhalation device. Nebulized aqueous suspensions or solutions are prepared with or without a suitable pH and/or tonicity adjustment.

RNA encoding a picornavirus 3Dpol polypeptide is administered to a mammal such as a human in any amount, at any frequency, and for any duration effective to achieve a desired outcome (e.g., to reduce a symptom of a picornavirus or a non-picornavirus such as a herpesvirus infection). In some cases RNA encoding a picornavirus 3Dpol polypeptide can be administered to a mammal to reduce a symptom of a picornavirus or herpesvirus infection by 5, 10, 25, 50, 75, 100, or more percent. Any appropriate method is used to determine whether or not a symptom of a viral infection is reduced. For example, a motor function test, or walking ability, is used for poliomyelitis or observation of appetite and weight increase as well as decreased malaise and sores is used for foot and mouth disease. In some cases, a nucleic acid encoding a picornavirus 3Dpol polypeptide is administered to a mammal to reduce the severity or to delay the onset of a severe viral infection (e.g., a severe picornavirus infection).

An effective amount RNA encoding a picornavirus 3Dpol polypeptide is any amount that reduces a symptom of a viral infection (e.g., a picornavirus or herpesvirus infection) without producing significant toxicity to a mammal. In some cases, the effective amount of RNA encoding a picornavirus 3Dpol polypeptide is between 0.1 µg/kg and 750 µg/kg (e.g., between 1 µg/kg and 500 µg/kg, between 10 µg/kg and 500 µg/kg, between 100 µg/kg and 500 µg/kg, between 1 µg/kg and 250 µg/kg, between 1 µg/kg and 100 µg/kg, between 10 µg/kg and 400 µg/kg, between 10 µg/kg and 250 µg/kg). If a particular mammal fails to respond to a particular amount, then the amount is increased by, for example, ten fold. After receiving this higher concentration, the mammal is monitored for both responsiveness to the treatment and toxicity symptoms, and adjustments made accordingly. The effective amount remains constant or is adjusted as a sliding scale or variable dose depending on the mammal's response to treatment (e.g., the mammal's level of picornavirus 3Dpol RNA or polypeptides or the mammal's state of infection).

Various factors can influence the actual effective amount used for a particular application. For example, the frequency of administration, duration of treatment, use of multiple treatment agents, route of administration, and severity of the viral infection (e.g., picornavirus or herpesvirus infection) requires an increase or decrease in the actual effective amount administered.

The frequency of administration of RNA encoding a picornavirus 3Dpol polypeptide is any frequency that reduces severity of a symptom of a viral infection (e.g., a picornavirus infection or a non-picornavirus infection such as herpesvirus infection) without producing significant toxicity to the mammal. For example, the frequency of administration is from about three times a day to about twice a month, or from about once a week to about once a month, or from about once every other day to about once a week, or from about once a month to twice a year, or from about four times a year to once every five years, or from about once a year to once in a lifetime. The frequency of administration remains constant or is variable during the duration of treatment. For example, a nucleic acid encoding a picornavirus 3Dpol polypeptide is administered daily, twice a day, five days a week, or three days a week. A nucleic acid encoding a picornavirus 3Dpol polypeptide is administered for five days, 10 days, three weeks, four weeks, eight weeks, 48 weeks, one year, 18 months, two years, three years, or five years. In some cases, RNA is administered as needed. A course of treatment includes rest periods. For example, RNA encoding a picornavirus 3Dpol polypeptide is administered for five days followed by a nine-day rest period, and such a regimen is repeated multiple times. As with the effective amount, various factors influence the actual frequency of administration used for a particular application. For example, the effective amount, duration of treatment, use of multiple treatment agents, route of administration, and severity of the viral infection may require an increase or decrease in administration frequency.

An effective duration for administering RNA, provided herein is any duration that reduces the severity of a symptom of a viral infection (e.g., a picornavirus infection or a non-picornavirus infection such as a herpesvirus infection) or achieves a particular level of nucleic acid (e.g., RNA) or picornavirus 3Dpol polypeptide expression without producing significant toxicity to the mammal. Thus, the effective duration varies from several days to several weeks, months, or years. In general, the effective duration for the treatment of a viral infection ranges in duration from several days to several weeks or longer. In some cases, an effective duration is for several months to a year. Multiple factors influence the actual effective duration used for a particular treatment. For example, an effective duration varys with the frequency of administration, effective amount, use of multiple treatment agents, route of administration, and severity of the viral infection.

Any appropriate method is used to determine whether or not an administered RNA results in an increased level of the nucleic acid and/or an increased level of picornavirus 3Dpol RNA or polypeptide. Any appropriate method is used to determine whether or not administered RNA encoding a picornavirus 3Dpol polypeptide (or fragment thereof) results in an increased level of the encoded polypeptide or polypeptide fragment within a mammal. For example, picornavirus 3Dpol polypeptide levels are detected using any standard antibody based assays such as immunoprecipitation, western hybridization, and sandwich enzyme-linked immunosorbent assays (ELISA). Antibody based assays utilize combinations of antibodies that bind to one or more sites of the amino-terminal, central, and carboxy-terminal portions of a picornavirus 3Dpol polypeptide. In some cases, the level of a picornavirus 3Dpol transcript is determined by measuring RNA levels using any appropriate method such as northern blotting, quantitative RT-PCR, microarray analysis, or in situ hybridization.

Example 4

Catalytically-Active 3Dpol Polypeptide Upregulates Antiviral Effectors

Figure 8A:
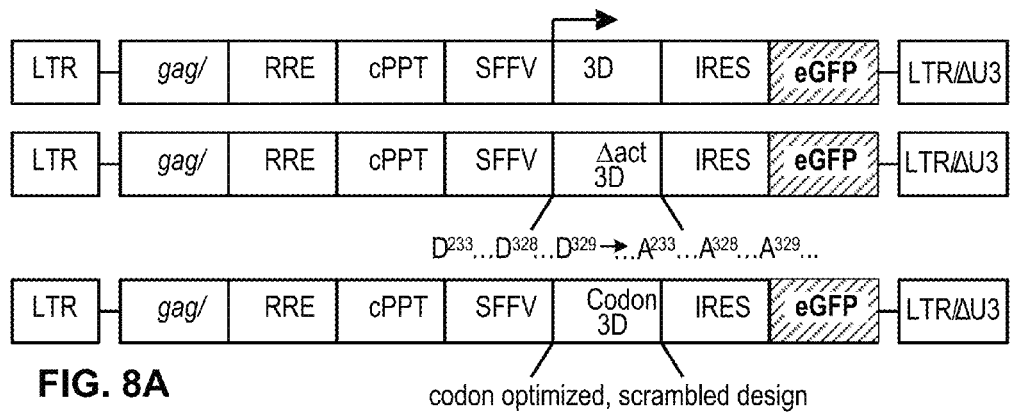
Figure 8B:
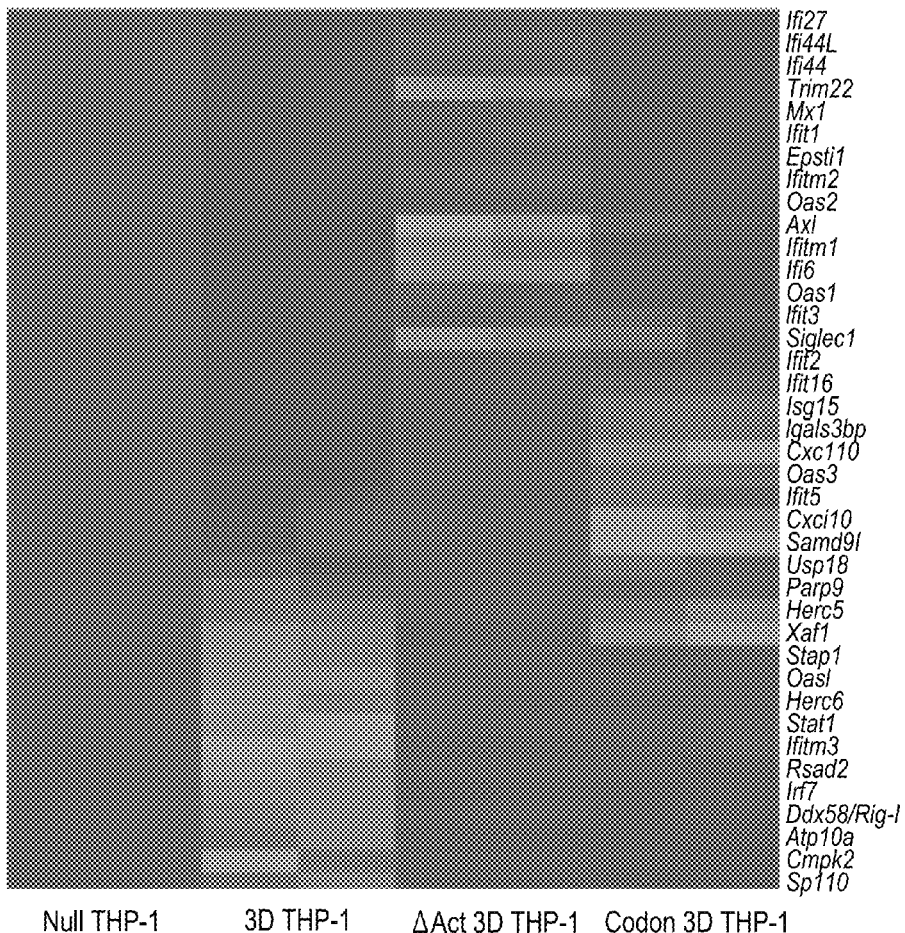

Using lentiviral vectors, human THP-1 cells (monocyte cell line) were designed to express (a) nucleic acid encoding a catalytically-active picornavirus 3Dpol polypeptide, (b) nucleic acid encoding a picornavirus 3Dpol polypeptide lacking the active site of the polymerase, or (c) a codon optimized nucleic acid encoding a picornavirus 3Dpol polypeptide that lacks secondary transcript (RNA) structure. The human cells expressing nucleic acid encoding a catalytically-active picornavirus 3Dpol polypeptide and codon optimized nucleic acid encoding a picornavirus 3Dpol polypeptide exhibited up to 500-fold increases in the expression of antiviral effectors, while the empty-vector control THP-1 cells (null) and THP-1 cells designed to express nucleic acid encoding a picornavirus 3Dpol polypeptide lacking the active site of the polymerase did not (FIG. 8).

These results demonstrate that 3Dpol polypeptides with catalytic activity can be used to increase expression of a set of nucleic acids encoding polypeptides involved in innate immunity within a mammal. Administration of nucleic acids (encoding 3Dpol polypeptides) or direct administration of 3Dpol polypeptides can be used to increase expression of a set of nucleic acids encoding polypeptides involved in innate immunity within a mammal.

Example 5

3Dpol Inhibits Viral Replication in Human Cells

A human cell line (designated 3D THP-1 cells) was engineered to express a picornavirus 3Dpol polypeptide under the control of a Spleen Focus-Forming Virus (SFFV) promoter by transducing THP-1 cells with a lentiviral vector. Stably-expressing cells were selected using puromycin (the lentiviral vectors expressed a puromycin-resistance gene). Once obtained, the 3D THP-1 cells were assessed for transgene incorporation by DNA sequencing.

To assess the ability of human cells expressing a picornavirus 3Dpol polypeptide to inhibit viral replication, the 3D THP-1 cells were exposed to escalating doses of engineered HIV virus expressing a red fluorescent protein (HIVred). THP-1 cells lacking picornavirus 3Dpol polypeptide expression were used as a control. Exposure of the control cells to HIVred resulted HIV infection (assessed by presence or absence of red fluorescent protein expression). The 3D THP-1 cells, however, resulted in significantly reduced HIVred infection as compared to the control THP-1 cells.

These results demonstrate the expression of a picornavirus 3Dpol polypeptide in human cells can be used to increase the ability of those cells to inhibit replication of human viruses. Administration of nucleic acids encoding 3Dpol polypeptides or direct administration of 3Dpol polypeptides can be used to increase expression of a set of nucleic acids encoding polypeptides involved in innate immunity within a mammal.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing expression of an Ifit1 polypeptide within a mammal, wherein said method comprises administering lentivirus particles comprising nucleic acid encoding a picornavirus 3Dpol polypeptide or a catalytically active fragment thereof to said mammal under conditions wherein expression of said Ifit1 polypeptide is increased, wherein said mammal is a mouse, dog, cat, cow, horse, or human.

2. The method of claim 1, wherein said mammal is a human.

3. The method of claim 1, wherein said picornavirus 3Dpol polypeptide comprises the amino acid sequence set forth in SEQ ID NO:2.

4. The method of claim 1, wherein said administering comprises an oral administration.

5. The method of claim 1, wherein said administering comprises an intravenous administration.

6. The method of claim 1, wherein said administering comprises a nasal inhalation.

7. The method of claim 1, wherein said lentiviral vector comprises nucleic acid encoding a fragment of said picornavirus 3Dpol polypeptide that is between 100 and 470 amino acid residues in length.

\* \* \* \* \*

SEQUENCE LISTING

```
<160> NUMBER OF SEQ ID NOS: 3

<210> SEQ ID NO 1
<211> LENGTH: 1419
<212> TYPE: DNA
<213> ORGANISM: Picornavirus

<400> SEQUENCE: 1
atgggtgcca tcgtagacat ttccacagga tctgttgtgc atgtccccag aaagaccaaa      60
ttgaggagaa cagtcgctca tgatgttttc caacccaaat tcgaacctgc agtgctgtca     120
cgctatgacc ctcggactga taaggacgtt gatgttgtag ctttttccaa acacaccact     180
aacatggaaa gcttgccccc ggtctttgat atcgtctgtg atgaatacgc taaccgcgtc     240
ttcactatcc ttggtaaaga caacggtctt ctgaccgttg aacaggccgt gcttggcttg     300
ccaggtatgg accccatgga gaaggacacc tctcctggat tgccctacac tcaacaagga     360
cttagacgaa ccgaccttct ggatttcaac actgctaaaa tgacacctca attggactac     420
gcccattcca aattggtgct cggcgtctat gacgacgtcg tctaccaatc atttttgaaa     480
gatgaaattc gacccttgga gaagatccac gaagcaaaaa cccggattgt tgacgtaccc     540
ccgtttgctc actgcatttg ggggaagacag cttctgggac gttttgcctc caaattccag     600
accaaacccg gactcgaact cggatctgca attggaactg acccggacgt tgattggaca     660
cgctacgccg ctgagctgag tgggttcaat tacgtctatg atgtagatta ctccaacttt     720
gatgcttccc attctactgc aatgtttgaa tgcttgatca agaatttctt cacagagcaa     780
aatggatttg acagacgcat tgccgagtat ctcagatcct tggctgtgtc gcgacatgct     840
tacgaggacc gccgtgtcct tatacgtgga ggcttgcctt cgggctgcgc tgccaccagc     900
atgttaaaca ccatcatgaa caatgttata attcgtgctg ccctgtacct tacctactca     960
aattttgaat ttgatgatat taaggtcctt tcctatggag atgacctttt aattggaact    1020
aattaccaaa ttgatttcaa tcttgttaaa gaaagattag ccccccttcgg ttataagatt    1080 actcctgcca acaagaccac cacctttccc ctgacctccc atttgcaaga tgttaccttt    1140
ctaaagagga gatttgtgag attcaattcc tacctgttta gacctcaaat ggatgctgtc    1200
aacttgaaag caatggttag ctactgtaaa ccaggaacac ttaaagagaa actaatgtcc    1260
attgctcttc tggccgttca ctccggacca gatatatatg atgagatttt cctgcccttt    1320
aggaatgttg gaatagttgt ccctacctat agttctatgc tttatagatg gcttagctta    1380
tttagacgtg atatcaccgg tcatcatcac catcaccat                           1419
```

```
<210> SEQ ID NO 2
<211> LENGTH: 473
<212> TYPE: PRT
<213> ORGANISM: Picornavirus

<400> SEQUENCE: 2

Met Gly Ala Ile Val Asp Ile Ser Thr Gly Ser Val Val His Val Pro
 1               5                  10                  15

Arg Lys Thr Lys Leu Arg Arg Thr Val Ala His Asp Val Phe Gln Pro
            20                  25                  30

Lys Phe Glu Pro Ala Val Leu Ser Arg Tyr Asp Pro Arg Thr Asp Lys
        35                  40                  45

Asp Val Asp Val Val Ala Phe Ser Lys His Thr Thr Asn Met Glu Ser
    50                  55                  60

Leu Pro Pro Val Phe Asp Ile Val Cys Asp Glu Tyr Ala Asn Arg Val
65                  70                  75                  80

Phe Thr Ile Leu Gly Lys Asp Asn Gly Leu Leu Thr Val Glu Gln Ala
                85                  90                  95

Val Leu Gly Leu Pro Gly Met Asp Pro Met Glu Lys Asp Thr Ser Pro
            100                 105                 110

Gly Leu Pro Tyr Thr Gln Gln Gly Leu Arg Arg Thr Asp Leu Leu Asp
        115                 120                 125

Phe Asn Thr Ala Lys Met Thr Pro Gln Leu Asp Tyr Ala His Ser Lys
    130                 135                 140

Leu Val Leu Gly Val Tyr Asp Asp Val Val Tyr Gln Ser Phe Leu Lys
145                 150                 155                 160

Asp Glu Ile Arg Pro Leu Glu Lys Ile His Glu Ala Lys Thr Arg Ile
                165                 170                 175

Val Asp Val Pro Pro Phe Ala His Cys Ile Trp Gly Arg Gln Leu Leu
            180                 185                 190

Gly Arg Phe Ala Ser Lys Phe Gln Thr Lys Pro Gly Leu Glu Leu Gly
        195                 200                 205

Ser Ala Ile Gly Thr Asp Pro Asp Val Asp Trp Thr Arg Tyr Ala Ala
    210                 215                 220

Glu Leu Ser Gly Phe Asn Tyr Val Tyr Asp Val Asp Tyr Ser Asn Phe
225                 230                 235                 240

Asp Ala Ser His Ser Thr Ala Met Phe Glu Cys Leu Ile Lys Asn Phe
                245                 250                 255

Phe Thr Glu Gln Asn Gly Phe Asp Arg Arg Ile Ala Glu Tyr Leu Arg
            260                 265                 270

Ser Leu Ala Val Ser Arg His Ala Tyr Glu Asp Arg Arg Val Leu Ile
        275                 280                 285

Arg Gly Gly Leu Pro Ser Gly Cys Ala Ala Thr Ser Met Leu Asn Thr
    290                 295                 300

Ile Met Asn Asn Val Ile Ile Arg Ala Ala Leu Tyr Leu Thr Tyr Ser
305                 310                 315                 320

Asn Phe Glu Phe Asp Asp Ile Lys Val Leu Ser Tyr Gly Asp Asp Leu
                325                 330                 335

Leu Ile Gly Thr Asn Tyr Gln Ile Asp Phe Asn Leu Val Lys Glu Arg
            340                 345                 350

Leu Ala Pro Phe Gly Tyr Lys Ile Thr Pro Ala Asn Lys Thr Thr Thr
        355                 360                 365

Phe Pro Leu Thr Ser His Leu Gln Asp Val Thr Phe Leu Lys Arg Arg
    370                 375                 380
```

```
Phe Val Arg Phe Asn Ser Tyr Leu Phe Arg Pro Gln Met Asp Ala Val
385                 390                 395                 400

Asn Leu Lys Ala Met Val Ser Tyr Cys Lys Pro Gly Thr Leu Lys Glu
            405                 410                 415

Lys Leu Met Ser Ile Ala Leu Leu Ala Val His Ser Gly Pro Asp Ile
        420                 425                 430

Tyr Asp Glu Ile Phe Leu Pro Phe Arg Asn Val Gly Ile Val Val Pro
        435                 440                 445

Thr Tyr Ser Ser Met Leu Tyr Arg Trp Leu Ser Leu Phe Arg Arg Asp
        450                 455                 460

Ile Thr Gly His His His His His His
465                 470
```

<210> SEQ ID NO 3
<211> LENGTH: 1419
<212> TYPE: RNA
<213> ORGANISM: Picornavirus

<400> SEQUENCE: 3

```
augggugcca ucguagacau uccacagga ucuguugugc augucccag aaagaccaaa     60
uugaggagaa cagucgcuca ugauguuuuc caacccaaau cgaaccugc agugcuguca   120
cgcuaugacc cucggacuga uaaggacguu gauguuguag cuuuuuccaa acacaccacu   180
aacauggaaa gcuugccccc ggucuuugau aucgucugug augaauacgc uaaccgcguc   240
uucacuaucc uugguaaaga caacggucuu cugaccguug aacaggccgu gcuuggcuug   300
ccagguaugg accccaugga aaggacacc ucuccuggau ugcccuacac ucaacaagga   360
cuuagacgaa ccgaccuucu ggauuucaac acugcuaaaa ugacaccuca auuggacuac   420
gcccauucca aauggugcu cggcgucuau gacgacgucg cuaccaauc auuuuugaaa   480
gaugaaauuc gacccuugga gaagauccac gaagcaaaaa cccggauugu ugacguaccc   540
ccguuugcuc acugcauuug gggaagacag cuucugggac guuugccuc caaauuccag   600
accaaacccg gacucgaacu cggaucugca auuggaacug acccgacgu ugauuggaca   660
cgcuacgccg cugagcugag uggguucaau uacgucuaug augagauua cucccaacuuu   720
gaugcuuccc auucuacugc aauguuugaa ugcuugauca gaauuucuu acagagcaa   780
aauggauuug acagacgcau ugccaguau cucagaucu uggcuguguc gcgacaugcu   840
uacgaggacc gccguguccu uauacgugga ggcuugccuu cgggcugcgc ugccaccagc   900
auguuaaaca ccaucaugaa caauguuaua auucgucugug cccuguaccu uaccacuca   960
aauuuugaau uugaugauau uaaggccuuu uccuauggag augaccuuuu aauuggaacu  1020
aauuaccaaa uugauuuuca ucuuguuaaa gaaagauuag ccccccuucgg uuauaagauu  1080
acuccugcca acaagaccac caccuuuccc cugaccucc auuugcaaga guuaccuuu   1140
cuaaagagga gauuugugag auucaauucc uaccuguuua gaccucaaau ggaugcuguc  1200
aacuugaaag caauugguag cuacuguaaa ccaggaacac uuaaagagaa acuaaugucc  1260
auugcucuuc uggccguuca cuccggacca gauauaugug augagauuuu ccugcccuuu  1320
aggaauguug gaauaguugu cccuaccuau agucuaugc uuauagaug gcuuaagcuua  1380
uuuagacgug auaucaccgg ucaucaucac caucaccau                         1419
```